United States Patent
Kojima et al.

(10) Patent No.: US 11,852,294 B2
(45) Date of Patent: Dec. 26, 2023

(54) DIAGNOSIS SYSTEM OF LUBRICATING OIL AND DIAGNOSIS METHOD OF LUBRICATING OIL

(71) Applicant: Hitachi, Ltd., Tokyo (JP)

(72) Inventors: Kyoko Kojima, Tokyo (JP); Mitsuru Saeki, Tokyo (JP); Shinichiro Aikawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 2 days.

(21) Appl. No.: 17/638,414

(22) PCT Filed: Oct. 15, 2020

(86) PCT No.: PCT/JP2020/038978
§ 371 (c)(1),
(2) Date: Feb. 25, 2022

(87) PCT Pub. No.: WO2021/095436
PCT Pub. Date: May 20, 2021

(65) Prior Publication Data
US 2022/0316653 A1    Oct. 6, 2022

(30) Foreign Application Priority Data
Nov. 13, 2019   (JP) .............................. 2019-205210

(51) Int. Cl.
*F16N 29/00*   (2006.01)
*F03D 80/70*   (2016.01)
(Continued)

(52) U.S. Cl.
CPC ............ *F16N 29/00* (2013.01); *F03D 80/70* (2016.05); *G01N 21/27* (2013.01); *G01N 33/30* (2013.01); *F05B 2260/98* (2013.01)

(58) Field of Classification Search
CPC .... F16N 90/00; F16N 2210/025; F03D 80/70; F05B 2260/98; F01N 33/2888
See application file for complete search history.

(56) References Cited

U.S. PATENT DOCUMENTS 6,061,139 A * 5/2000 Takezawa .......... G01N 21/3151
356/70
9,724,995 B2 * 8/2017 Ozaki .................... B60L 53/16
(Continued)

FOREIGN PATENT DOCUMENTS

JP    61-248999 A    11/1986
JP    2002-276537 A    9/2002
(Continued)

OTHER PUBLICATIONS

International Search Report of PCT/JP2020/038978 dated Dec. 8, 2020.
(Continued)

*Primary Examiner* — Michael A Riegelman
(74) *Attorney, Agent, or Firm* — MATTINGLY & MALUR, PC

(57) ABSTRACT

Provided is a diagnosis technique with high reliability when a state of lubricating oil of a rotary machine such as a wind power generator is diagnosed by a state monitoring sensor. A diagnosis system of lubricating oil includes a lubricating oil utilization device, a lubricating oil tank for storing lubricating oil to be supplied to the lubricating oil utilization device, and a sensor which measures characteristics of the lubricating oil. In this system, the state of the lubricating oil is diagnosed by using sensor data obtained after a time required for air bubbles in the lubricating oil generated at the time of use of the device disappear elapses since the lubricating oil utilization device is regularly or irregularly stopped.

15 Claims, 21 Drawing Sheets

(51) Int. Cl.
*G01N 21/27* (2006.01)
*G01N 33/30* (2006.01)

(56) References Cited

U.S. PATENT DOCUMENTS

| | | | |
|---|---|---|---|
| 9,746,452 B2* | 8/2017 | Worden | G01M 13/02 |
| 10,018,613 B2* | 7/2018 | Potyrailo | G01N 33/2888 |
| 10,746,680 B2* | 8/2020 | Potyrailo | G01N 27/026 |
| 11,209,357 B2* | 12/2021 | Kojima | G01N 21/51 |
| 2010/0001526 A1* | 1/2010 | Fukuda | F03D 17/00 290/44 |
| 2013/0250303 A1* | 9/2013 | Shirata | B25J 13/087 356/436 |
| 2013/0342150 A1* | 12/2013 | Ozaki | F16H 57/0476 318/490 |
| 2014/0103652 A1* | 4/2014 | Ubben | F03D 7/048 290/44 |
| 2014/0363290 A1* | 12/2014 | Jacobsen | F03D 17/00 416/61 |
| 2016/0252448 A1* | 9/2016 | Ida | G01N 21/255 356/70 |
| 2017/0138876 A1* | 5/2017 | Potyrailo | G01N 33/2847 |
| 2020/0025177 A1* | 1/2020 | Redding | F03D 7/00 |
| 2020/0292450 A1* | 9/2020 | Kojima | G01N 21/78 |
| 2020/0355163 A1* | 11/2020 | Kojima | G01N 33/2888 |
| 2021/0054824 A1* | 2/2021 | Ishimitsu | F03D 17/00 |
| 2022/0316653 A1* | 10/2022 | Kojima | G01N 33/2858 |

FOREIGN PATENT DOCUMENTS

| | | |
|---|---|---|
| JP | 2004-176796 A | 6/2004 |
| JP | 2008-184932 A | 8/2008 |
| JP | 2008-267866 A | 11/2008 |
| JP | 2011-053075 A | 3/2011 |
| JP | 2011-127723 A | 6/2011 |
| JP | 2012-117951 A | 6/2012 |
| JP | 2012-189095 A | 10/2012 |
| JP | 2017-198717 A | 11/2017 |
| JP | 2017-219325 A | 12/2017 |
| JP | 2019-078718 A | 5/2019 |
| WO | 2018/207464 A1 | 11/2018 |

OTHER PUBLICATIONS

German Office Action received in corresponding German Application No. 11 2020 004 305.3 dated Jul. 7, 2023.

* cited by examiner

DIAGNOSIS SYSTEM OF LUBRICATING OIL AND DIAGNOSIS METHOD OF LUBRICATING OIL

TECHNICAL FIELD

The present invention relates to a diagnosis technique for a rotary machine, and particularly to a deterioration diagnosis technique for lubricating oil used in a speed increasing machine of a wind power generator and a state diagnosis technique for the speed increasing machine, a lubricating oil diagnosis technique for the rotary machine such as an air compressor, a ship, and a power generation turbine, and a state diagnosis technique for the machine.

BACKGROUND ART

In order to perform protection and maintenance of large-scaled rotary machines, property diagnosis of lubricating oil used in rotating parts such as bearings and gears is an important technique. Examples of the large-scaled rotary machine include a speed increasing machine of a wind power generator, an air compressor, a ship, and a power generation turbine. In the property diagnosis of the lubricating oil, diagnosis is performed for two types roughly classified into (1) oxidation deterioration of the lubricating oil over time and (2) contamination due to external contaminants such as water, dust, and abrasion powder.

(1) As the oxidation deterioration of the lubricating oil, there are deteriorations due to oxidation of base oil and deterioration due to consumption of an additive, or the like. The oxidation deterioration of the lubricating oil causes a decrease in abrasion resistance, changes in viscosity and viscosity index, a decrease in rust prevention property, a decrease in corrosion prevention property, and the like. As a result, abrasion and material fatigue of the speed increasing machine may be promoted.

(2) The contamination of the lubricating oil occurs due to water, dust, abrasion powder resulting from rotating parts, and the like. Water mixing causes deterioration in lubricating performance due to a change in viscosity of the lubricating oil, corrosion and rust of metal parts, and deterioration in a material. Dust itself is less likely to cause a fatal failure, but may cause an increase in metal abrasion powder. It is known that the abrasion powder causes a fatal machine failure depending on a size thereof.

A small amount of lubricating oil of the rotary machine such as the speed increasing machine is collected at a predetermined cycle and is sent to an analysis center or the like. Viscosity, a degree of contamination, a total acid value, a metal concentration, and the like may be analyzed, and properties of the lubricating oil may be monitored. State monitoring by a sensor group (for example, sensors of an output, a power generator rotational speed, a power generation amount, an oil temperature, a hydraulic pressure, and an acceleration) installed in the wind power generator is performed.

In the related art, as the property diagnosis technique of the lubricating oil, for example, there is a technique described in PTL 1. PTL 1 discloses that a type of a contaminant in the lubricating oil is specified based on a color detected by an optical sensor.

CITATION LIST

Patent Literature

PTL 1: JP 2012-117951 A

SUMMARY OF INVENTION

Technical Problem

The lubricating oil includes various additives in order to maintain lubricating performance. For example, when a lubrication condition is severe and a pressure at a contact portion is high or when a sliding speed is low or the viscosity of the oil is too low, a film of the lubricating oil between friction surfaces becomes thin, frictional resistance increases, and abrasion occurs. This state is called boundary lubrication, and seizure occurs in an extreme case. The additives serve to reduce friction and abrasion in such a state of boundary lubrication, and are, for example, oiliness agents, abrasion prevention agents, and extreme pressure additives (extreme pressure agents). These additives may be collectively referred to as load-bearing additives. Other additives include antioxidants and antifoaming agents. It is necessary for the additive to be contained in the lubricating oil at a predetermined ratio (concentration) in order to maintain desired lubricating performance.

In the related art, as a deterioration diagnosis of the lubricating oil, a technique for detecting deterioration due to a contaminant by light transmission has been proposed as described in PTL 1. PTL 1 describes that since the color of light which is out of white light emitted by a white light emitting element and has a wavelength that is not absorbed by the contaminant in the lubricating oil in an oil gap is detected by a color light receiving element, the color of the contaminant in the lubricating oil of the machine can be immediately detected (paragraph 0009).

However, the air bubbles are likely to be generated in the lubricating oil of the machine being operated due to stirring, cavitation, or the like. Thus, when a state of the lubricating oil is diagnosed by detecting the color, the light is scattered at an interface between the lubricating oil as a liquid and the air bubbles, and sensor data changes depending on the amount, size, and the like of the air bubbles.

Since the sensor data obtained when the machine is stopped as planned, such as at the time of periodic inspection, is data in a state where there are almost no air bubbles, the sensor data may be accurate data. However, in the case of the wind power generator or the like in which a frequency of planned stoppage is not high, there is a problem that a measurement interval is too wide and diagnosis cannot be performed at a necessary frequency.

A particle counter is known as another example of the sensor. The particle counter measures particles by an electric signal when light is scattered or blocked by the particles, but in principle, it is not possible to measure oxidation and consumption of the additive. When the air bubbles are generated in the lubricating oil, since the particle counter measures a shadow of reference light transmitted through the lubricating oil, in principle, it is difficult to distinguish between the air bubbles and solid particles.

As another example of the sensor, in a method for measuring electrical characteristics such as dielectric constant and electrical conductivity of the lubricating oil, there is a problem that apparent sensor data changes due to the air bubbles contained in the lubricating oil.

The wind power generator needs to perform a stable operation at a high level and needs to have a power generation amount, and reliability to withstand long-term use from 20 years to 25 years. Thus, the wind power generator needs to have a predictive diagnosis function of detecting abnormality before abnormality such as a failure occurs, and needs to reduce downtime. Since an expensive part such as the speed increasing machine is used, the wind power generator needs to prevent a failure in advance by predictive diagnosis. Thus, it is necessary to know the state of the lubricating oil with high accuracy on a site. However, in lubricating oil having high viscosity such as a speed increasing machine lubricating oil of a wind turbine, since the air bubbles are easily generated and hardly disappear, it is necessary to eliminate or consider the influence of the air bubbles when the state of the lubricating oil is measured.

Since the lubricating performance of the lubricating oil deteriorates due to the consumption of the additive, it is necessary to regularly replace the lubricating oil. However, since it is necessary to stop the operation in order to replace the lubricating oil, a power generation amount loss occurs. The replacement of the lubricating oil requires new oil cost, waste oil cost, worker cost, and the like, and thus, the high cost of lubricating oil replacement has been a problem.

An object of the present invention is to provide a diagnosis technique with high reliability when a state of lubricating oil in a rotary machine such as a wind power generator is diagnosed by a state monitoring sensor.

Solution to Problem

A preferred aspect of the present invention is a diagnosis system of lubricating oil including a lubricating oil utilization device, a lubricating oil tank for storing lubricating oil to be supplied to the lubricating oil utilization device, a circulation line through which lubricating oil circulated between the lubricating oil tank and the lubricating oil utilization device flows, and a sensor which measures characteristics of the lubricating oil. Data of the sensor is acquired and is used for diagnosis after more than a predetermined time elapses since the lubricating oil utilization device enters a stoppage state.

Another preferred aspect of the present invention is a diagnosis system of lubricating oil including a lubricating oil utilization device, a lubricating oil tank for storing lubricating oil to be supplied to the lubricating oil utilization device, a circulation line through which lubricating oil circulated between the lubricating oil tank and the lubricating oil utilization device flows, and a chromaticity sensor which measures characteristics of the lubricating oil. Data of the sensor when a value of a deterioration index based on sensor data of the chromaticity sensor is in a predetermined range is acquired and is used for diagnosis.

Still another preferred aspect of the present invention is a diagnosis method of lubricating oil in an apparatus which includes a lubricating oil utilization device, a lubricating oil tank for storing lubricating oil to be supplied to the lubricating oil utilization device, and a circulation line through which lubricating oil circulated between the lubricating oil tank and the lubricating oil utilization device flows. The method includes using a chromaticity sensor which measures characteristics of the lubricating oil, and acquiring data of the chromaticity sensor and using the data for diagnosis after more than a predetermined time elapses since the lubricating oil utilization device enters a stoppage state.

Advantageous Effects of Invention

According to the present invention, it is possible to provide the diagnosis technique with high reliability when the state of the lubricating oil in the rotary machine such as the wind power generator is diagnosed by the state monitoring sensor. Other objects, configurations, and effects will be made apparent in the following descriptions.

DESCRIPTION OF EMBODIMENTS

In a wind power generator, lubricating oil or the like is used in order to reduce a mechanical friction coefficient between components. In the following embodiment, a lubricating oil monitoring technique will be described by using the lubricating oil of the wind power generator as an example. However, the present invention can be applied not only to the wind power generator but also to a turbine and other machines.

An example to be described in an embodiment is a diagnosis system of a wind power generator that collects information from the wind power generator having a speed increasing machine and a power generator and determines abnormality of the wind power generator based on the collected information. In this system, in order to monitor a state of the wind power generator, a sensor that outputs, as sensor information, properties of the lubricating oil to be supplied to the speed increasing machine, and a storage unit that stores a reference value defined for each sensor information are included.

<1. Basic Configuration of Wind Power Generator>

Figure 1:
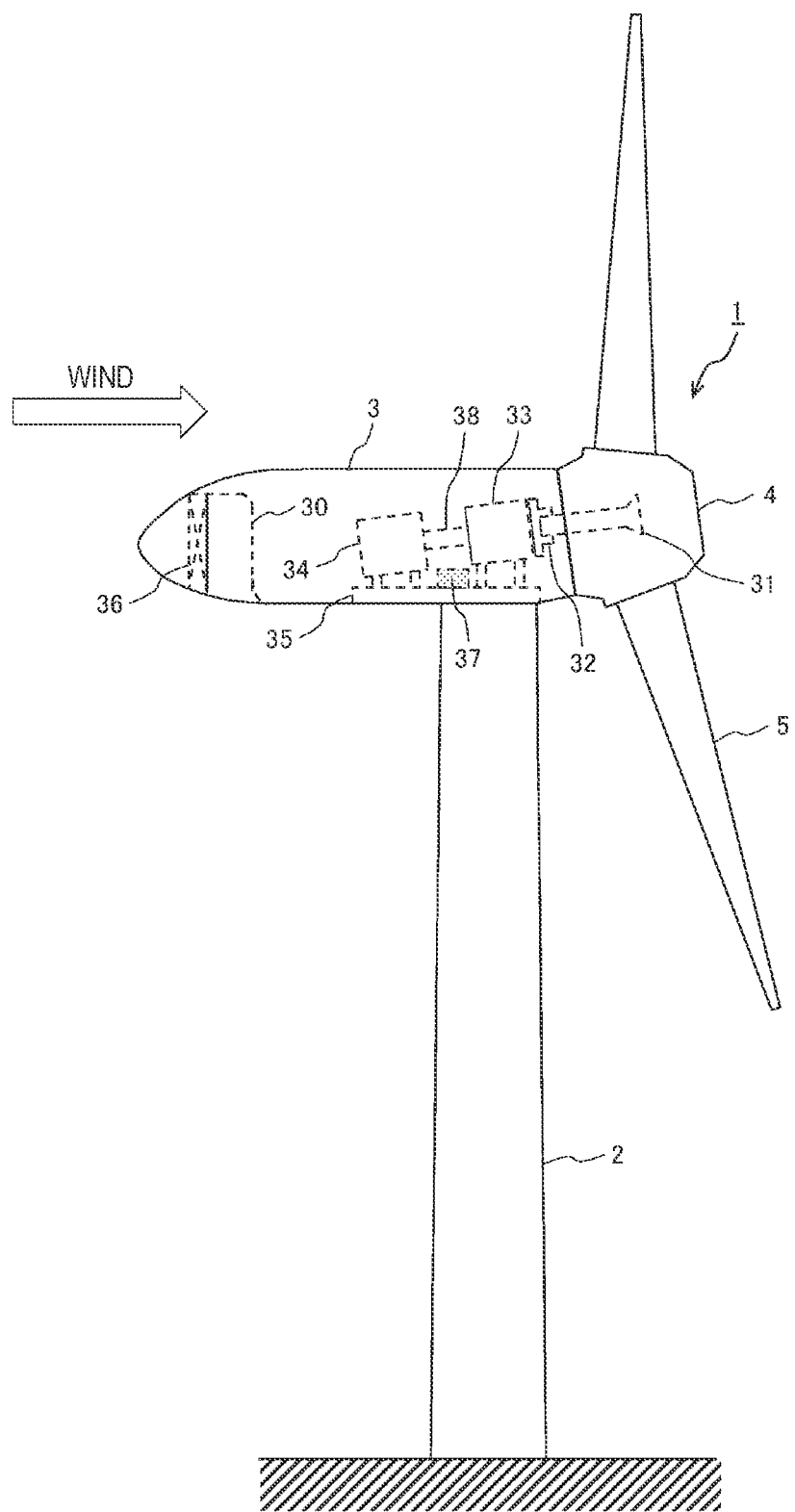
FIG. 1 is a schematic overall configuration diagram of a wind power generator.

FIG. 1 is a schematic overall configuration diagram of a downwind-type wind power generator. In FIG. 1, each device disposed in a nacelle 3 is indicated by a dotted line. As illustrated in FIG. 1, the wind power generator 1 includes blades 5 that rotate by receiving wind, a hub 4 that supports the blades 5, a nacelle 3, and a tower 2 that rotatably supports the nacelle 3 in a horizontal plane.

The nacelle 3 includes a main shaft 31 that is connected to the hub 4 and rotates together with the hub 4, a shrink disk 32 that is coupled to the main shaft 31, a speed increasing machine 33 that is connected to the main shaft 31 with the shrink disk 32 interposed therebetween and increases a rotational speed, and a power generator 34 that rotates a rotor at the rotational speed increased by the speed increasing machine 33 with a coupling 38 interposed therebetween and performs a power generation operation.

A unit that transmits rotational energy of the blades 5 to the power generator 34 is called a power transmission unit, and the main shaft 31, the shrink disk 32, the speed increasing machine 33, and the coupling 38 are included in the power transmission portion. The speed increasing machine 33 and the power generator 34 are held on a main frame 35. One or a plurality of lubricating oil tanks 37 for storing lubricating oil for lubricating the power transmission unit are installed on the main frame 35. In the nacelle 3, a radiator 36 is disposed on a windward side of a nacelle partition wall 30. Cooling water cooled by the radiator 36 by using outside air is circulated through the power generator 34 and the speed increasing machine 33 to cool the power generator 34 and the speed increasing machine 33. In FIG. 1, although a so-called downwind-type wind turbine has been described as an example, it goes without saying that the present embodiment can be applied to an upwind-type wind turbine.

In the wind power generator, the lubricating oil is used in many rotary machines. For example, in FIG. 1, the lubricating oil is supplied to the main shaft 31, the speed increasing machine 33, the power generator 34, and bearings such as yaw and pitch (not illustrated). Control for changing and outputting a pitch angle in the blades according to a wind speed is pitch control of the blades, and azimuth control of the nacelle that causes a direction of the wind turbine to follow the wind direction in order to receive the wind without waste is yaw control.

In addition to such a power transmission unit, a rotary machine including the rotary machine for performing the yaw control or the pitch control needs to supply the lubricating oil by forced circulation. The lubricating oil reduces friction of a rotating portion of the rotary machine, and prevents wear, breakage, or energy loss of parts. However, when deterioration in lubricating performance due to deterioration of the lubricating oil over time or contamination due to mixing of abrasion particles, dust, and the like into the lubricating oil occurs, a friction coefficient increases, and a failure risk of the wind power generator increases.

When the wind power generator fails, since a large loss cost occurs, such as a cost for replacement of a failed component and a decrease in power generation revenue during a power failure, measures such as early parts procurement by remaining lifespan prediction and sign detection and shortening of a power failure period are desired. In particular, in the speed increasing machine which is an important component, when the performance of the lubricating oil decreases, since a failure risk increases, a technique for estimating a remaining lifespan or a replacement time of the lubricating oil as early as possible is important.

<2. Method for Evaluating Characteristics of Lubricating Oil>

As a method for evaluating characteristics of the lubricating oil or the like, inductively coupled plasma (ICP) elemental analysis and component analysis by liquid chromatography mass spectrometry (LC/MS) (hereinafter, referred to as LC measurement) or the like can be performed. However, in general, in the LC measurement or the like, it is necessary to obtain a sample, carry the sample to an experimental facility, and process the sample, and it is difficult to perform evaluation on a site. Thus, it is conceivable to measure optical properties and electrical properties of the sample on the site and indirectly measure the properties of the lubricating oil. As described above, as a measurement method, there are various methods such as a method for evaluating the color of the lubricating oil, a method for evaluating the electrical characteristics such as dielectric constant and electrical conductivity, and a method for optically measuring mixed particles (for example, see PTL 1 and known literatures cited therein). However, in many measurement methods, air bubbles in the lubricating oil influence the measurement result.

Hereinafter, an example in which a concentration of an additive of the lubricating oil is measured by using chromaticity data obtained based on measurement data of an optical sensor will be described. In an oiliness agent, an abrasion prevention agent, an extreme pressure additive, an antioxidant, an antifoaming agent, and the like, which are additives, there is often a correlation between the additive concentration and the chromaticity, and the concentration can be evaluated. As a result of examination by the inventors, it has been found that there is a correlation between the concentration of the additive in the lubricating oil used in a machine having a rotating part such as a wind turbine and a degree of coloration (chromaticity) of the lubricating oil which are obtained by the LC measurement or the like.

Figure 2:
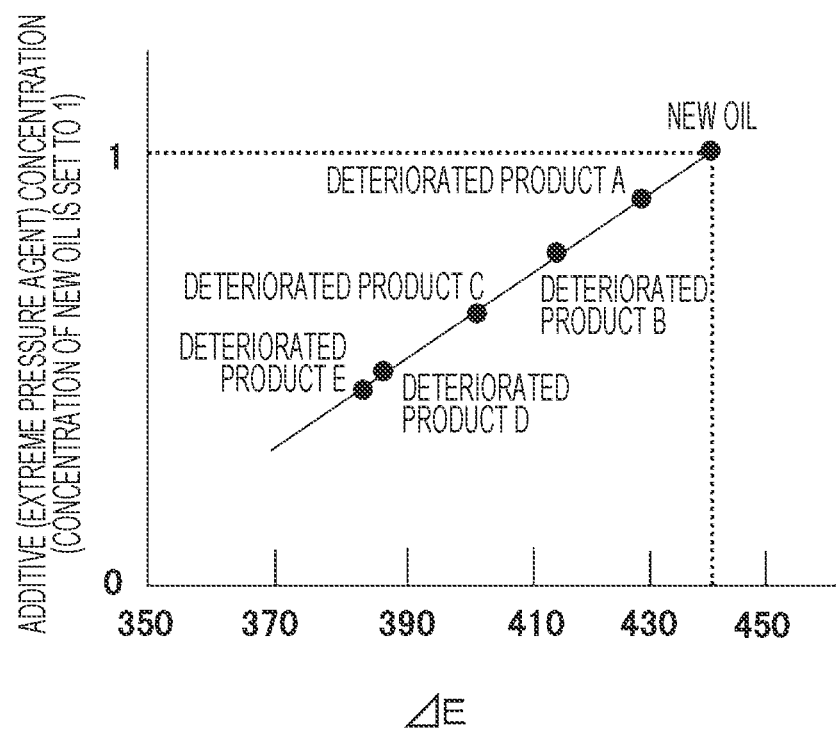
FIG. 2 is a graph representing a correlation between a concentration and chromaticity of an additive (extreme pressure agent) in lubricating oil.

FIG. 2 is a diagram illustrating a correlation between the concentration and the chromaticity of the extreme pressure agent in the lubricating oil. A vertical axis indicates the concentration of the additive in the lubricating oil obtained by the LC measurement or the like, and a horizontal axis indicates the chromaticity obtained based on the measurement data of the optical sensor. Here, in FIG. 2, the chromaticity is represented by a color difference ($\Delta E$) calculated in a color space constituted by a combination of RGB.

The definition of $\Delta E$ in FIG. 2 is as follows $$\Delta E = (R^2 + G^2 + B^2)^{1/2},$$

and R, G, and B mean three primary colors (red, green, blue) of light in additive mixing, and are expressed as (R, G, B) in numerical display of color coordinates. Wavelengths of the three primary colors of light are R from 610 nm to 750 nm, G from 500 nm to 560 nm, and B from 435 nm to 485 nm.

RGB chromaticity encoded with 24 bpp (24 bits per pixel) is represented by an integer (0 to 255) of three 8-bit codes indicating luminance of red, green, and blue. For example, (0, 0, 0) indicates black, (255, 255, 255) indicates white, (255, 0, 0) indicates red, (0, 255, 0) indicates green, and (0, 0, 255) indicates blue. In addition to the RGB color system, there are many types of chromaticity display such as an XYZ color system, an L*a*b* color system, and an L*u*v* color system. Since these color systems can be mathematically converted and developed into various color systems, chromaticity may be displayed in another color system. When the color of the lubricating oil is quantified in terms of chromaticity, an original color of the lubricating oil can be displayed on a monitor or a display of a computer or a monitoring system by converting a chromaticity value.

For each additive, when a relationship between the concentration of the additive in the lubricating oil used in the machine having the rotating part such as the wind turbine which is obtained by the LC measurement or the like and the chromaticity of the lubricating oil used in the machine having the rotating part such as the wind turbine which is obtained based on the measurement data of the optical sensor is obtained in advance as illustrated in FIG. 2, the chromaticity of the lubricating oil obtained based on the measurement data of the optical sensor can be obtained at the time of monitoring the lubricating oil, and the concentration of the additive of the lubricating oil can be measured based on the chromaticity of the lubricating oil.

As described above, it has become clear that a decrease (degree of consumption) of the additive in the lubricating oil which is an index of the deterioration in the lubricating oil is obtained from the chromaticity measured by the optical sensor. Accordingly, it is possible to easily measure the concentration of the additive in the lubricating oil as compared with the analysis by the LC measurement, Fourier transform infrared spectroscopy (FT-IR), nuclear magnetic resonance (NMR), or the like. When the optical sensor or the like is installed in the nacelle, online remote monitoring of the lubricating oil of the wind power generator can be performed. As in this example, when the characteristics of the lubricating oil are evaluated from the chromaticity of the lubricating oil, it is necessary to accurately measure the chromaticity, and it is necessary to reduce the influence of the air bubbles.

In FIG. 2, although a case where the extreme pressure agent is contained as the additive in the lubricating oil, as the additive, an antioxidant and an antifoaming agent can also be similarly used in addition to an oiliness agent, an abrasion prevention agent, and an extreme pressure additive which are load-bearing additives.

Figure 3:
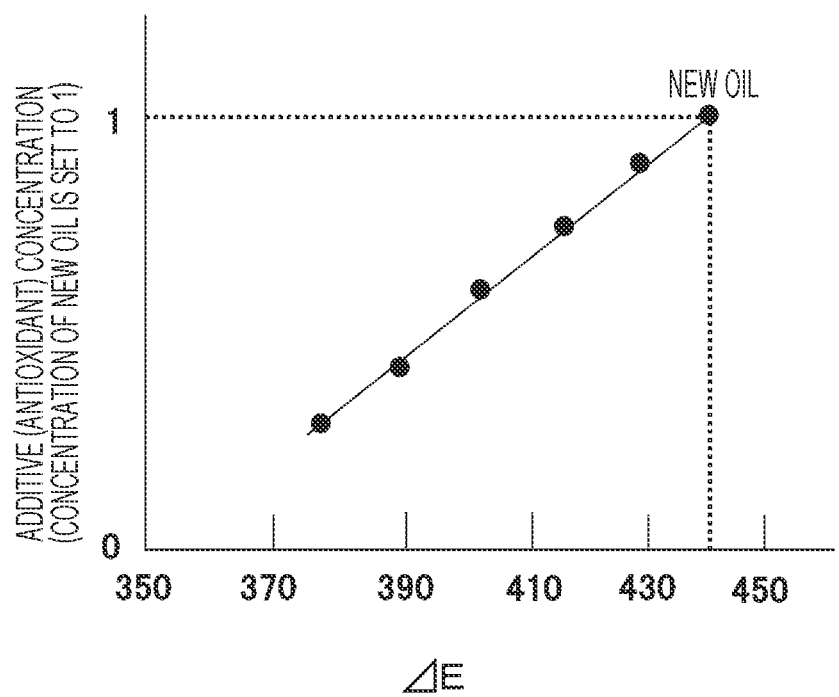
FIG. 3 is a graph representing a correlation between a concentration and chromaticity of an additive (antioxidant) in the lubricating oil.

FIG. 3 illustrates a correlation between the concentration and the chromaticity of the antioxidant in the lubricating oil as one example thereof.

The reason why the degree of consumption of the additive which is the index of deterioration in the lubricating oil correlates with the chromaticity is described as follows. When the additive acts on a sliding surface of a gear or a bearing, the additive is decomposed. A decomposition product of the additive is an oxidation product such as a phenolic oxide or quinone, and is colored in yellow to reddish brown. For example, when butylated hydroxytoluene (BHT) which is an antioxidant or triphenyl phosphorothionate (TPPT) which is an extreme pressure agent is decomposed, a colored compound is generated. BHT or TPPT before oxidation is almost colorless. From these factors, the deterioration in the lubricating oil is positively correlated with an increase in the colored compound which is the decomposition product. Accordingly, a degree of deterioration in the lubricating oil is obtained by chromaticity measurement.

The lubricating oil may include multiple additives. In this case, when the relationship between the concentration of each additive in the lubricating oil used in the machine having the rotating part such as the wind turbine which is obtained by the LC measurement or the like and the chromaticity of the lubricating oil which is obtained based on the measurement data of the optical sensor is obtained in advance and a calibration curve is created, the concentration of each additive in the lubricating oil can also be measured based on the chromaticity of the lubricating oil which is obtained based on the measurement data of the optical sensor at the time of monitoring the lubricating oil.

The calibration curve indicating the relationship between the degree of deterioration and the chromaticity of the lubricating oil can also be created by using the lubricating oil forcibly oxidatively deteriorated by various oxidation tests known as a deterioration acceleration test of the lubricating oil. Even though a type of the additive and an initial concentration are the same, when a type of base oil is different, a degree of change in the chromaticity due to deterioration associated with the use in the machine may be different. Thus, it is necessary to create the calibration curve indicating the relationship between the degree of deterioration and the chromaticity of the lubricating oil for each oil type.

Figure 4:
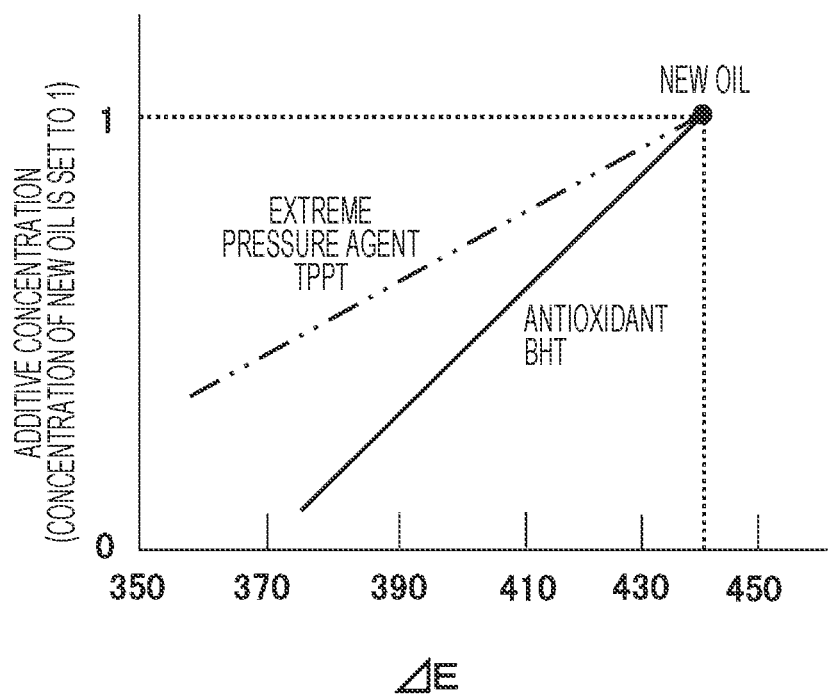
FIG. 4 is a graph representing a correlation between concentrations and chromaticity of two kinds of additives in the lubricating oil.

FIG. 4 is a diagram illustrating the correlation between the additive concentration and the chromaticity of the additive in the lubricating oil in which two kinds of the extreme pressure agent (TPPT) and the antioxidant (BHT) are blended, as the additives, with a certain amount. As can be seen from this drawing, the concentrations of additives having different consumption rates such as the extreme pressure agent and the antioxidant can also be measured based on the chromaticity obtained based on the measurement data of the optical sensor.

The present inventors have found that it is possible to distinguish between the consumption (deterioration) of the additives of the lubricating oil and the contamination of the lubricating oil based on measurement data of the optical sensor. When the lubricating oil is contaminated with dust, water, abrasion particles generated from the machine, or the like, the dust and the abrasion particles are solid contents, and the water is dispersed without being dissolved in the lubricating oil. Thus, the additive of the lubricating oil can be detected by the optical sensor by using the fact that a light transmittance decreases independently of the wavelength. When the contamination of the lubricating oil occurs, since the measurement data of the optical sensor mainly exhibits a behavior different from the deterioration in the lubricating oil due to the consumption of the additive, a degree of contamination of the lubricating oil can be measured by a degree of deviation of the deterioration from the calibration curve.

When the deterioration and contamination of the lubricating oil are minor and the lubricating oil replacement and part replacement are not necessary, it is not necessary to stop the wind power generator, collect the lubricating oil from the speed increasing machine of the wind power generator, and perform LC measurement, composition analysis such as FT-IR and NMR, element analysis, fine particle measurement, viscosity measurement, and total acid value analysis from the viewpoint of time and cost.

Thus, the properties of the lubricating oil are detected by various sensors including the optical sensor installed in the lubricating oil of the speed increasing machine, an extent of a degree of abnormality of the lubricating oil is discriminated in real time based on the sensor information (numerical value indicating a physicochemical state of the lubricating oil), and the collection of the lubricating oil for detailed lubricating oil analysis is prompted at an appropriate timing before the speed increasing machine fails according to the discrimination result. A relationship between the sensor information and the degree of abnormality (impurity concentration, degree of oxidation, or the like) of the lubricating oil is experimentally obtained in advance and stored as a database. Accordingly, it is possible to prevent a failure in advance by performing appropriate lubricating oil replacement, filter replacement, part replacement, or the like, and it is possible to efficiently manage the wind power generator by quickly performing a handling process such as repair.

As the lubricating oil properties that can be measured by a lubricating oil property sensor, there are temperature, chromaticity, viscosity, density, dielectric constant, electrical conductivity, and contamination grade (ISO code or NAS grade) of the lubricating oil. Since the lubricating oil properties measurable by each lubricating oil property sensor varies depending on the specification of the sensor (there are not only one sensor but also two or more sensors capable of measuring the lubricating oil properties), a combination of the lubricating oil property sensors actually mounted on the speed increasing machine varies depending on the lubricating oil properties to be measured and the specification of each sensor.

<3. Handling of Bubbles in Lubricating Oil>

When the lubricating oil is used in the machine having the rotating part such as a wind turbine, air bubbles are generated in the lubricating oil, and considerably influence sensor data for measuring the lubricating oil properties. In the case of the sensor that measures the contamination grade, since a shadow of a contaminating particle as a solid material when light passes through the lubricating oil is detected, when there are air bubbles in the lubricating oil, it is difficult to distinguish between a shadow of the air bubble from the shadow of the solid material, and a correct degree of contamination cannot be measured. In the case of the sensor that measures physical properties such as viscosity, density, dielectric constant, and electrical conductivity, since air having greatly different physical property values is contained in a certain volume of lubricating oil, correct measurement cannot be performed when there are air bubbles in the lubricating oil. In the case of the optical sensor that obtains the chromaticity by measuring a visible light transmittance of the lubricating oil, since light is reflected at an interface between the air bubbles in the lubricating oil and the lubricating oil, a correct light transmittance cannot be measured.

Accordingly, when the lubricating oil in the wind turbine being operated is measured by the sensor, it is effective to install the sensor at a place where the number of air bubbles is smaller or to remove the air bubbles by additional means in order to perform accurate measurement. Alternatively, it is very effective to install the sensor in the wind turbine and to perform accurate measurement when the wind turbine is stopped irregularly.

Figure 5:
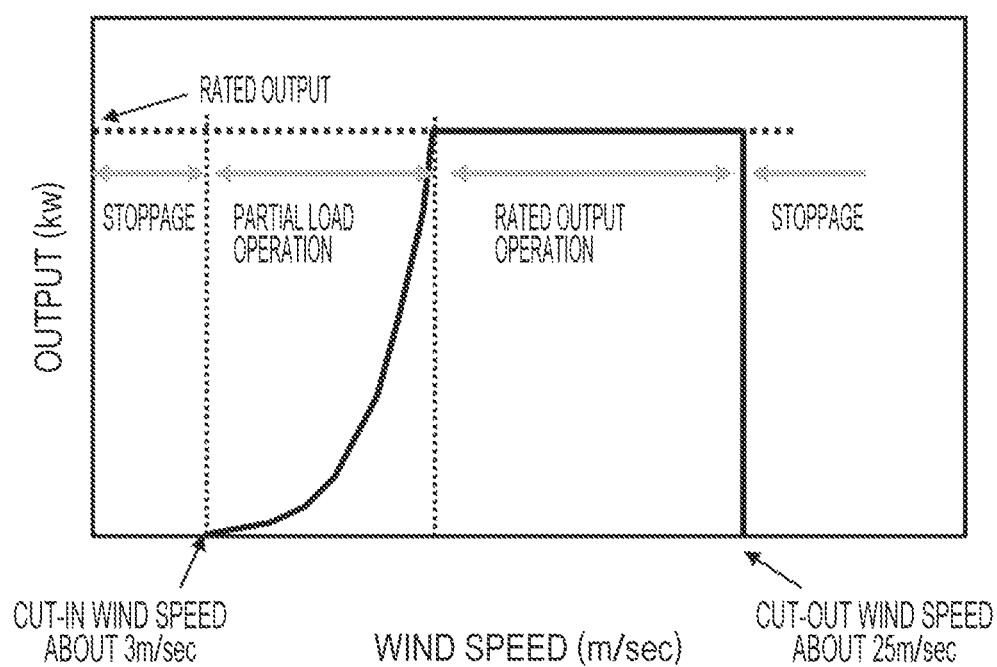
FIG. 5 is a graph of a power curve of the wind power generator.

FIG. 5 is a graph representing the wind speed on a horizontal axis and an output of the wind power generator on a vertical axis. As represented in a power curve of the wind power generator of FIG. 5, in power generation control of the wind turbine, a cut-in wind speed (about 2 m/s to 3 m/s) and a cut-out wind speed (about 25 m/s) are set, power generation is started when the wind speed exceeds the cut-in wind speed, and power generation is stopped when the wind speed exceeds the cut-out wind speed. In the case of strong wind, the power generation is stopped by setting the blades to be parallel to the wind direction. As described above, the rotary machine or the like may be brought into an unexpected stoppage state due to external factors such as wind conditions.

According to the examination of the inventors, the air bubbles in the lubricating oil disappear when the rotation of the speed increasing machine or the like is substantially stopped, that is, when a power generation amount is substantially zero. Whether or not the speed increasing machine is substantially stopped may be determined based on, for example, whether or not the rotational speed of the speed increasing machine or the like falls below a predetermined threshold value.

The power generation amount is substantially zero when the wind speed is equal to or less than the cut-in wind speed, when the wind speed is equal to or greater than the cut-out wind speed, when a failure occurs in the wind turbine or a transmission line, when the wind turbine is stopped for inspection and repair, and the like. However, even though the power generation amount is substantially zero when the wind speed is equal to or less than the cut-in wind speed, the rotor may rotate due to the low-speed wind, and accordingly, the speed increasing machine may rotate at a low speed with no load. In this case, since the wind speed is low, an air bubble amount in the lubricating oil is small.

The lubricating oil used in the speed increasing machine of the wind turbine has a composition close to a composition of gear oil containing the extreme pressure agent at a high concentration, and often has a relatively high viscosity of about VG320. VG is a viscosity grade defined by international standards, and subsequent numbers represent a viscosity index. As the numerical value becomes larger, the viscosity of the oil becomes higher.

Generally, the antifoaming agent is blended in the lubricating oil for the speed increasing machine, but a large amount of air bubbles are generated during operation of the speed increasing machine. Since the viscosity is high, a speed at which the air bubbles generated once disappear is slow, and it may take one hour or more after the speed increasing machine is stopped until the air bubbles in a portion close to an oil level disappear.

Generally, the wind turbine is controlled so as to perform optimum power generation according to a wind condition that constantly changes. A local wind direction and wind speed change drastically, and it is very difficult to predict the local wind direction and wind speed. Thus, even though the wind speed is not zero, the wind turbine may be temporarily stopped in order to control the power generation of the wind turbine. That is, in addition to planned stoppage of the wind turbine such as periodic inspection, unexpected stoppage of the speed increasing machine may frequently occur. Such unpredictable stoppage of the speed increasing machine due to an external factor may occur once or more per day. When the stoppage of the speed increasing machine for one hour or more which is necessary to eliminate the air bubbles of the speed increasing machine lubricating oil generated during operation occurs, accurate lubricating oil sensor data having no influence of the air bubbles can be obtained.

Hereinafter, embodiments of the present invention will be described in detail with reference to the drawings. However, the present invention is not interpreted as being limited to the description contents of the embodiments to be illustrated below. It is easily understood by those skilled in the art that the specific configuration can be changed without departing from the idea or the spirit of the present invention.

In a configuration of the invention to be described below, the same portions or portions having similar functions share the same reference signs in different drawings, and redundant descriptions may be omitted.

When there are a plurality of components having the same or similar functions, the same reference signs may be given with different subscripts. In this case, when there is no need to distinguish between the plurality of components, the description may be made while the subscripts are omitted.

Notations such as "first", "second", and "third" in the present specification are given to identify the components, and do not necessarily limit the number, order, or contents thereof. The numbers for identifying components are used for each context, and a number used in one context does not necessarily indicate the same configuration in another context. A component identified by a certain number is not hindered from also functioning as a component identified by another number.

Positions, sizes, shapes, and ranges of components illustrated in the drawings or the like may not necessarily represent actual positions, sizes, shapes, and ranges in order to facilitate understanding of the invention. Thus, the present invention is not necessarily limited to the positions, sizes, shapes, and ranges disclosed in the drawings.

In the following embodiments, there are provided a wind power generator that includes a speed increasing machine and a power generator, and a diagnosis system for a wind power generator that collects information from the wind power generator and determines abnormality of the wind power generator based on the collected information. An example in which more accurate sensor diagnosis is performed by using sensor data obtained at a timing at which the air bubbles are further reduced when properties of lubricating oil to be supplied to the speed increasing machine are measured and diagnosed by a sensor will be described.

FIRST EMBODIMENT

In a first embodiment, in order to monitor lubricating oil to be supplied to a mechanical drive unit of a wind power generator, an acceleration of a speed increasing machine for grasping properties of the lubricating oil and a state of the rotary machine is detected by various sensors including an optical sensor installed in the lubricating oil of the speed increasing machine, and an extent of a degree of abnormality of the lubricating oil and a state of a rotary machine are discriminated in real time based on the sensor information (numerical value indicating a physicochemical state of the lubricating oil). The diagnosis system for a wind power generator prompts lubricating oil collection, lubricating oil replacement, filter replacement, and part replacement for detailed lubricating oil analysis at an appropriate timing before the speed increasing machine fails according to the discrimination result. The system includes an input device, a processing device, a storage device, and an output device. The storage device stores a relative relationship between a concentration of an additive in the lubricating oil and chromaticity that is data of the optical sensor, and the processing device estimates a time at which the concentration of the additive in the lubricating oil obtained from chromaticity characteristics of the lubricating oil is equal to or less than a predetermined threshold value (reference value) based on the optical sensor data for measuring the chromaticity of the lubricating oil.

In the first embodiment, there are provided wind power generator diagnosis system and method that use an optical lubricating oil sensor and use a server including a processing device, a storage device, an input device, and an output device. In this method, first, in order to grasp the properties of the lubricating oil, a first step of acquiring chromaticity data of the lubricating oil of the wind power generator, a second step of measuring the additive concentration contained in the sample, a third step of storing the measured concentration of the additive in time series in the storage device to obtain additive concentration data, and a fourth step of processing the additive concentration data by the processing device to estimate the time at which the concentration of the additive reaches the predetermined threshold value are executed.

(1. Overall System Configuration)

Figure 6:
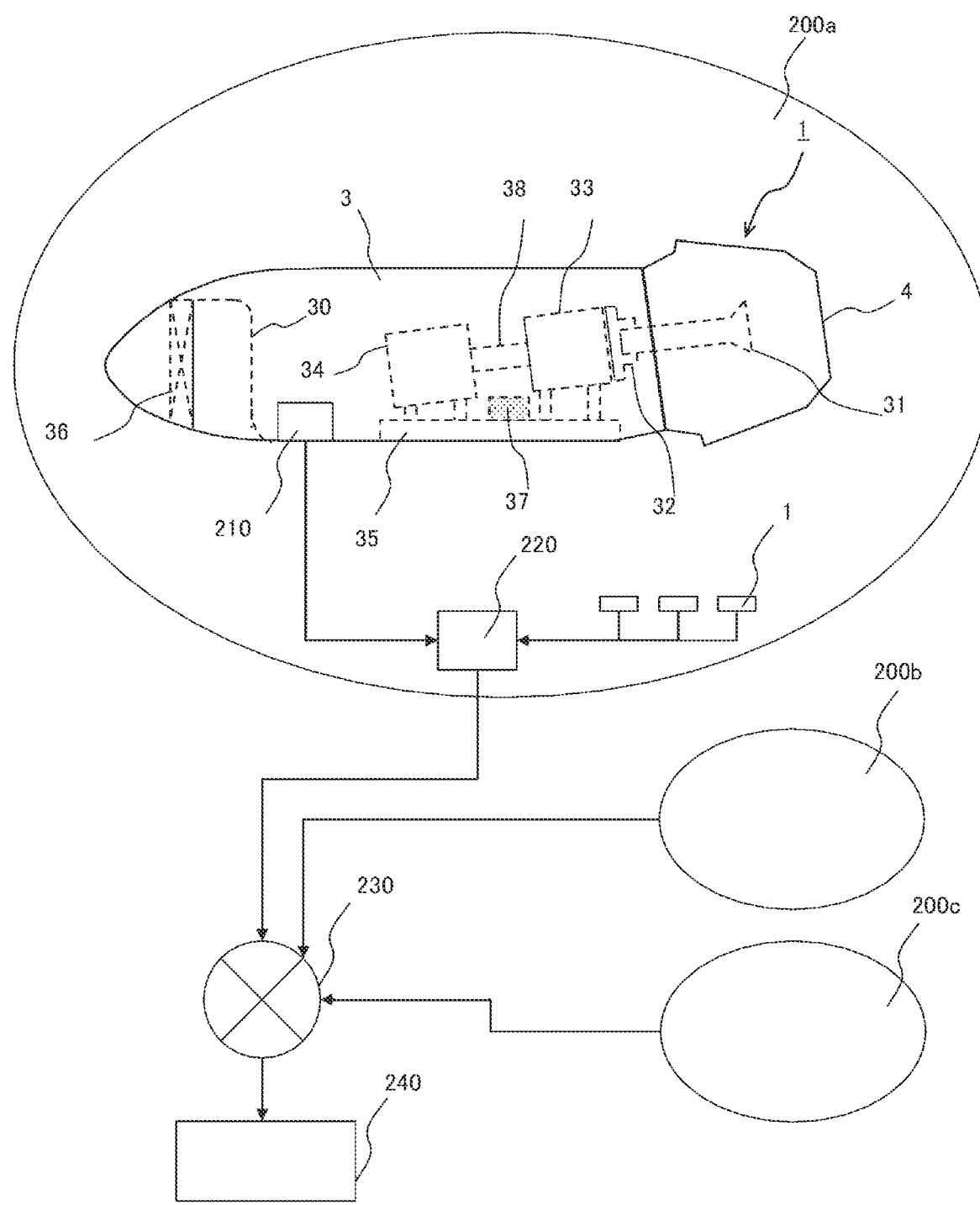
FIG. 6 is a schematic diagram of a monitoring system of the lubricating oil of the wind power generator having a lubricating oil supply system.

FIG. 6 is a schematic diagram of a monitoring system of the lubricating oil of the wind power generator having a lubricating oil supply system. In FIG. 6, a portion of the nacelle 3 of the wind power generator 1 of FIG. 1 is extracted and illustrated for the sake of description. Inside the nacelle 3, there are the main shaft 31, the speed increasing machine 33, the power generator 34, and the bearings such as yaw and pitch (not illustrated), and the lubricating oil is supplied from the lubricating oil tank 37 to these components.

As illustrated in FIG. 6, a plurality of wind power generators 1 are usually installed on the same site, and these wind power generators are collectively referred to as a farm 200*a* or the like. In each wind power generator 1, various sensors (not illustrated) are installed in the lubricating oil supply system, and sensor signals reflecting the state of the lubricating oil are collected in a server 210 in the nacelle 3. The sensor signal obtained from the server 210 of each wind power generator 1 is transmitted to an aggregation server 220 disposed for each farm. Data from the aggregation server 220 is sent to a central server 240 via a network 230. Data from other farms 200*b* and 200*c* is also sent to the central server 240. The central server 240 can send an instruction to each wind power generator 1 via the aggregation server 220 or the server 210.

(2. Sensor Arrangement)

Figure 7:
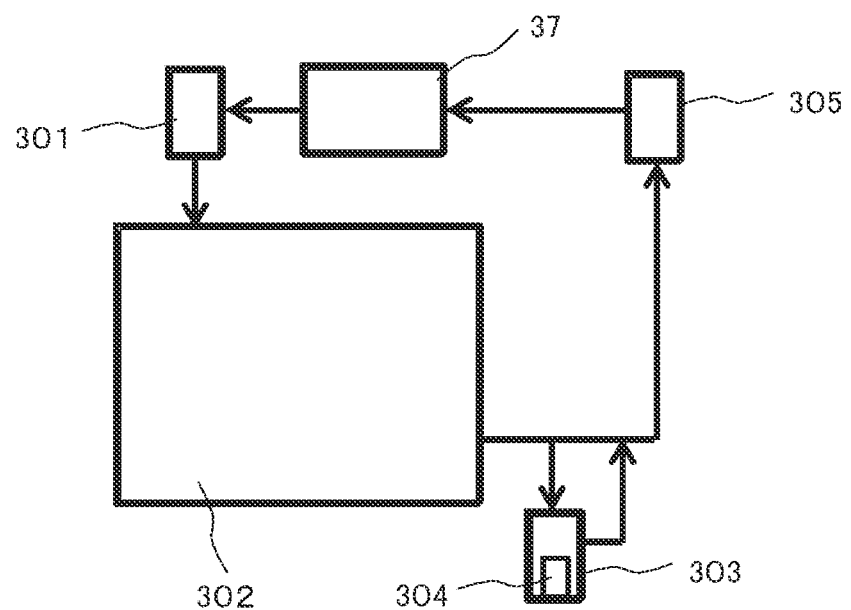
FIG. 7 is a configuration diagram of a rotary machine including a lubricating oil sensor according to a first embodiment.

FIG. 7 is a conceptual diagram of the rotary machine including a lubricating oil sensor. The lubricating oil is supplied from a lubricating oil supply device 301 such as a pump to a rotary machine 302. The lubricating oil supply device 301 is connected to the lubricating oil tank 37 and receives the supply of the lubricating oil. The rotary machine 302 may include, for example, a power transmission unit for performing yaw and pitch control in addition to the speed increasing machine 33 and other portions where mechanical contact occurs.

A sensor group 304 is arranged in a flow path of the lubricating oil or the like in order to detect the state of the lubricating oil. In the first embodiment, a measurement unit 303 is provided in a flow path (branch line) branched from the flow path of the lubricating oil connected to an oil discharge port of the lubricating oil of the rotary machine 302, a part of the lubricating oil is introduced into the measurement unit 303, and the sensor group 304 is installed in the measurement unit 303. The branch line is preferably provided near an end of the lubricating oil path in order to monitor a state of the deterioration in the lubricating oil. The measurement unit 303 is not provided in a main flow path (circulation line) of the lubricating oil in order to adjust a flow rate of the lubricating oil in the measurement unit 303 to a flow rate suitable for detecting the state of the lubricating oil. As described above, a hydraulic pressure can also be adjusted by adjusting a bent shape and a thickness of the branch line by using a branch line branched from the circulation line and disposed in parallel with the circulation line.

The lubricating oil discharged from the rotary machine 302 returns to the lubricating oil tank 37 via an oil filter 305. A mesh diameter of the oil filter 305 is 5 µm to 50 µm.

When a positional relationship along the flow path of the lubricating oil is expressed, the expression of upstream and downstream may be used. The lubricating oil relatively moves from upstream to downstream. In the case of FIG. 7, the lubricating oil supply device 301 is upstream, the oil filter 305 is downstream, and the measurement unit 303 is disposed therebetween. The arrangement of components is not limited to the configuration of FIG. 7, and for example, as will be described later, the lubricating oil tank 37 may be disposed between the rotary machine 302 and the measurement unit 303.

The sensor group 304 measures various parameters of the lubricating oil. For example, a physical quantity includes temperature, hydraulic pressure, and the like in addition to the chromaticity by the optical sensor. Instead of or in addition to the optical sensor, a sensor that measures electrical characteristics such as dielectric constant and electrical conductivity of the lubricating oil may be provided. The temperature, the hydraulic pressure, and the like can be measured by using a known sensor. The state of the lubricating oil can be evaluated based on temporal changes in these parameters. The sensor that measures the temperature and the like is not essential, but is preferably provided in order to detect the state of the lubricating oil in more detail.

In the first embodiment, the sensor group 304 includes an optical sensor including a visible light source and a light receiving element. The optical sensor measures a visible light transmittance of the lubricating oil, and outputs chromaticity information (values of R, G, and B) of the lubricating oil. The amount of the residual additive in the lubricating oil is obtained from the acquired chromaticity data, and diagnosis for a degree of deterioration and diagnosis for a remaining lifespan are performed. In the diagnosis by the sensor data, the diagnosis is performed based on the sensor data by the optical sensor or the optical sensor and other one or more types of sensor data.

The quality of the lubricating oil deteriorates due to the use and does not perform an initial function. Thus, it is necessary to perform maintenance such as replacement according to a state of the deterioration in the quality. In order to know a timing of such maintenance, it is useful to enable monitoring of data that can be collected by the sensor group 304 at a remote location in terms of efficiency of maintenance management. The data collected by the sensor group 304 is collected, for example, in the server 210 in the nacelle 3, and then sent to the central server 240 that aggregates data of a plurality of farms via the aggregation server 220 that aggregates data in the farm 200.

The aggregated data may include not only data related to the lubricating oil but also data indicating an operation status of the wind power generator. Examples thereof include an acceleration sensor that detects the vibration of the wind power generator 1 (the larger the value, the higher the deterioration rate of the lubricating oil), a wind turbine output value (the larger the value, the higher the deterioration rate of the lubricating oil), an actual operation time (the larger the value, the higher the deterioration rate of the lubricating oil), a machine temperature (the larger the value, the higher the deterioration rate of the lubricating oil), a rotational speed of the shaft (the larger the value, the higher the deterioration rate of the lubricating oil), and a temperature of the lubricating oil (the larger the value, the higher the deterioration rate of the lubricating oil). These data can be collected from sensors of known configurations installed in various location of the wind power generator and control signals of the device.

(3. Behavior of Air Bubbles in Lubricating Oil)

Figure 8:
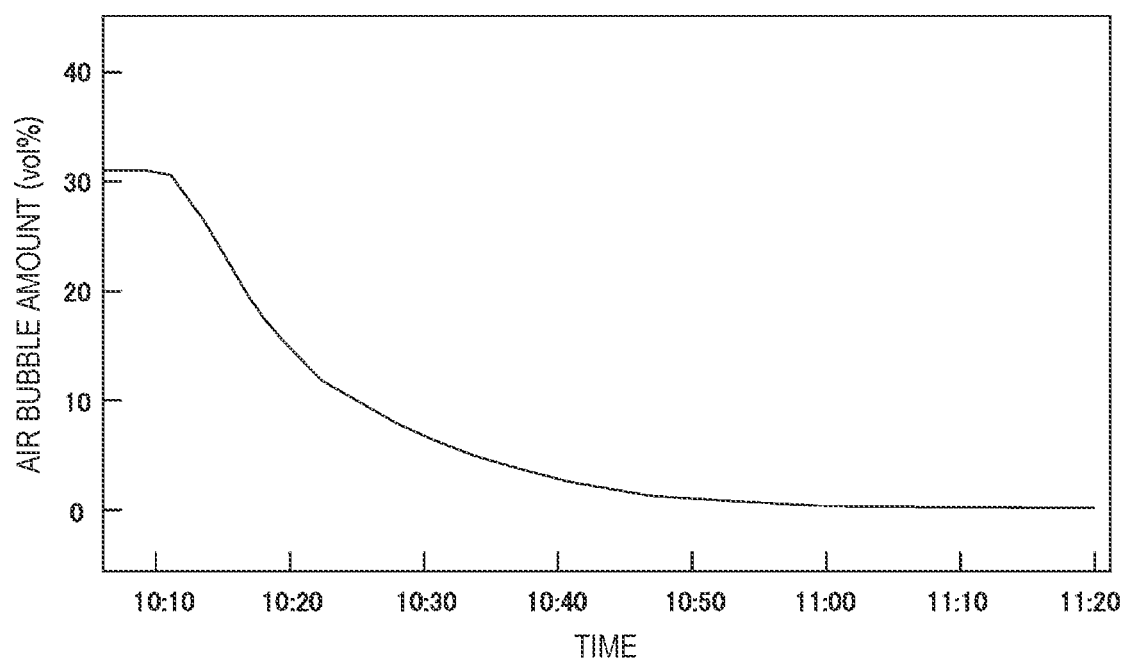
FIG. 8 is a graph representing that air bubbles in the lubricating oil decrease after a speed increasing machine is stopped.

FIG. 8 is a diagram illustrating a change in the air bubble amount in the speed increasing machine lubricating oil accompanying the operation and stoppage of the speed increasing machine of the 2 MW wind turbine. Power was generated at the rating until 10:10, but the speed increasing machine was stopped from 10:10. The air bubble amount in the lubricating oil of the speed increasing machine was about 30% in terms of volume ratio at the time of rated power generation, but reached 0% at 11:10 after one hour. The oil temperature at this time was 50° C. to 53° C. When the optical sensor measurement for measuring the color of the lubricating oil was performed in this speed increasing machine, the chromaticity of the lubricating oil exhibits a value lower than the original chromaticity until 11:00, and a value representing the original chromaticity of the lubricating oil was obtained after 11:00. That is, in this example, it can be seen that the influence of the air bubbles does not influence the measurement of the chromaticity sensor after 50 minutes from the stoppage of the rotary machine 302.

The behavior of the air bubble amount in the lubricating oil depends on the viscosity, temperature, and chemical composition of the lubricating oil, but the same behavior is exhibited even when a model of the wind turbine and a structure of the speed increasing machine are different.

(4. Relationship Between Wind Turbine Operation State, Air Bubble Amount, and Sensor Data)

Figure 9:
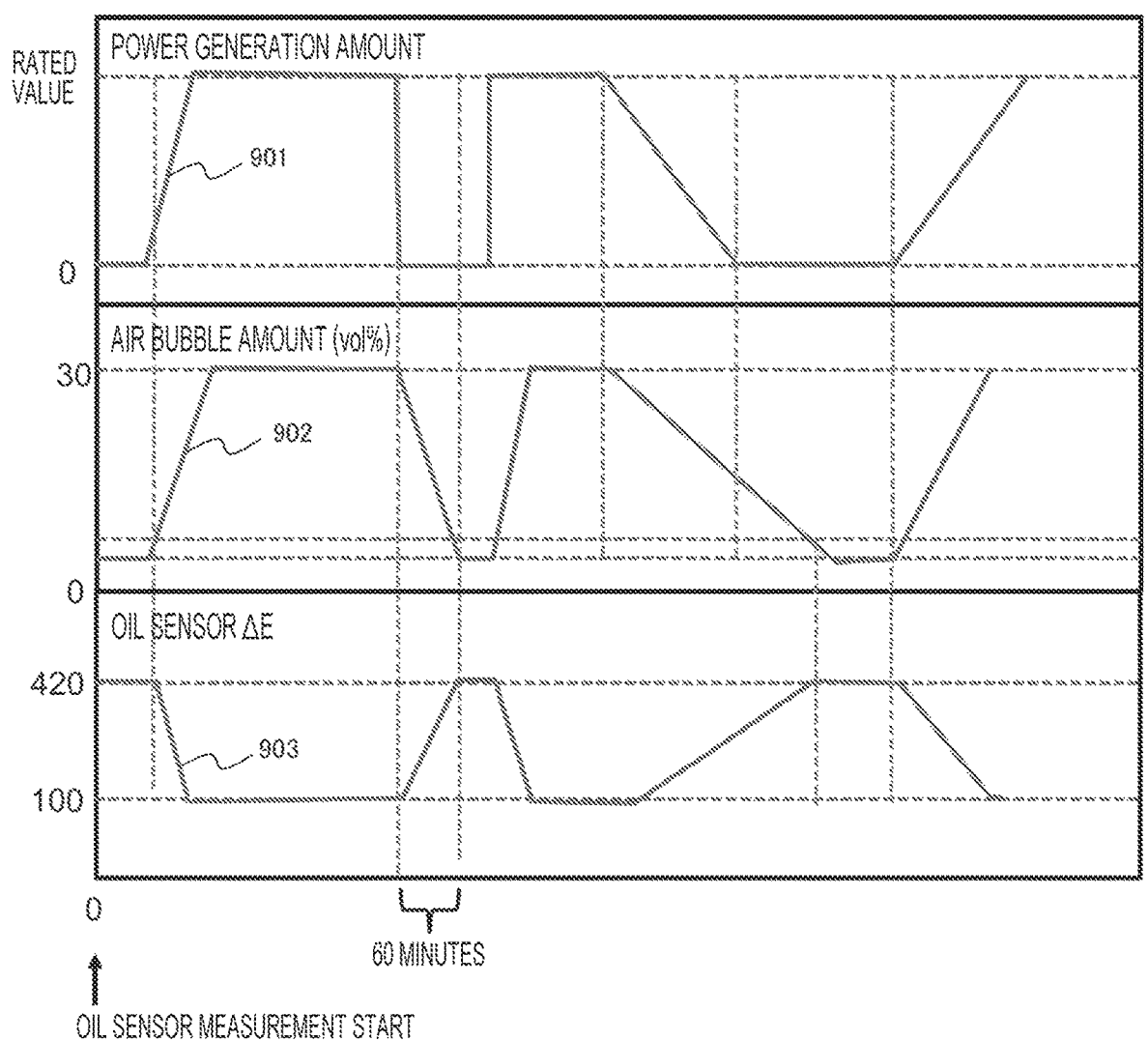
FIG. 9 is a graph representing a correlation among a wind turbine power generation amount, an air bubble amount in the lubricating oil, and an optical sensor $\Delta E$ value.

FIG. 9 illustrates a relationship between an operation state of the 2 MW wind turbine having the speed increasing machine, the air bubble amount in the speed increasing machine oil, and optical sensor data ΔE for measuring the speed increasing machine oil. A power generation amount 901 increased with the start of the power generation, an air bubble amount 902 in the oil increased, and oil sensor data ΔE 903 rapidly decreased from 420 which is an original value.

When the power generation was stopped, the air bubble amount gradually decreased, and accordingly, 60 minutes after the power generation was stopped, ΔE returned to 420 which is the original value. The deterioration diagnosis of the lubricating oil could be performed by using the optical sensor data after the lapse of 60 minutes from the power generation stoppage.

In general, for example, the fact that the power generation amount of the wind turbine indicates zero means, that is, that the speed increasing machine is stopped. In the case of a wind power plant, usually, the power generation amount of the wind turbine is measured by a supervisory control and data acquisition (SCADA) or the like. Since it could be confirmed that the operation state of the wind turbine and the air bubble amount in the speed increasing machine lubricating oil have a correlation with good reproducibility, when the power generation amount of the wind turbine is measured, it can be said that the air bubbles in the speed increasing machine oil are indirectly measured. The air bubbles in the lubricating oil can be directly measured by using a volume flowmeter and a mass flowmeter in combination.

Figure 10:
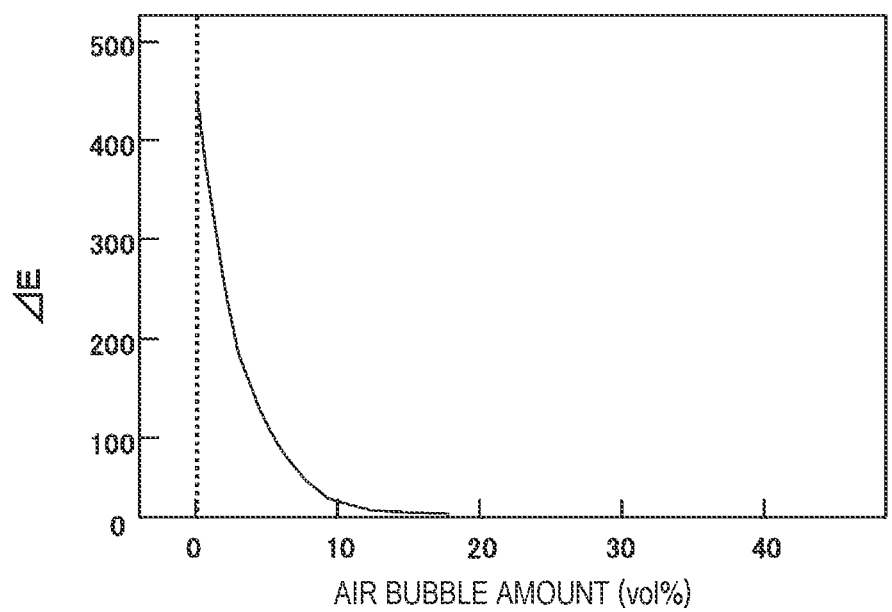
FIG. 10 is a graph representing a correlation between the air bubble amount in the lubricating oil and the $\Delta E$ value.

FIG. 10 is a diagram illustrating a relationship between the air bubble amount (vol %) in the lubricating oil of the speed increasing machine of the 2 MW wind turbine and the ΔE value obtained by the measurement by the optical sensor.

Figure 11:
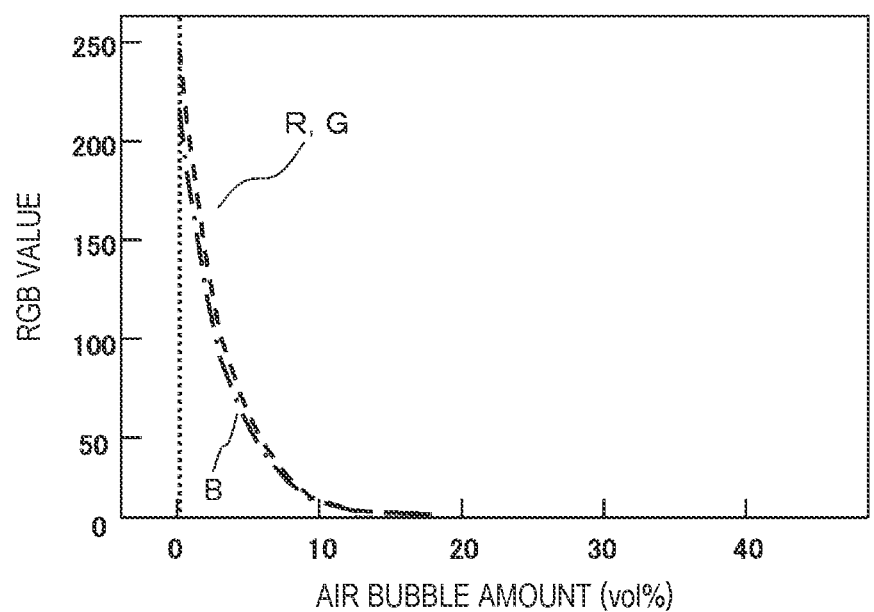
FIG. 11 is a graph representing a correlation between the air bubble amount in the lubricating oil and RGB values.

FIG. 11 is a diagram illustrating a relationship between the air bubble amount (vol %) in the lubricating oil of the speed increasing machine of the 2 MW wind turbine and the RGB values obtained by the measurement by the optical sensor.

Figure 12:
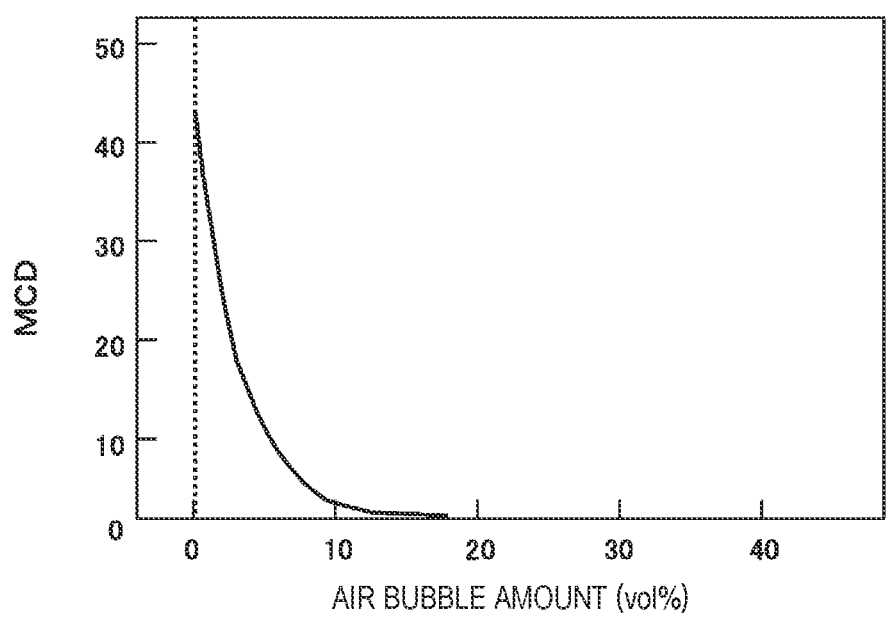
FIG. 12 is a graph representing a correlation between the air bubble amount in the lubricating oil and an MCD value.

FIG. 12 is a diagram illustrating a relationship between an air bubble amount (vol %) in lubricating oil of another speed increasing machine of the 2 MW wind turbine and an MCD value obtained by the measurement by the optical sensor. In this wind turbine, 3.5 years have elapsed since the replacement of the lubricating oil, and the deterioration in the lubricating oil has progressed to a moderate level. The MCD stands for Maximum Color Difference, and means a maximum color difference. In oil diagnosis, a difference between R and B is usually used.

(5. Flow of Lubricating Oil Diagnosis)

Figure 13:
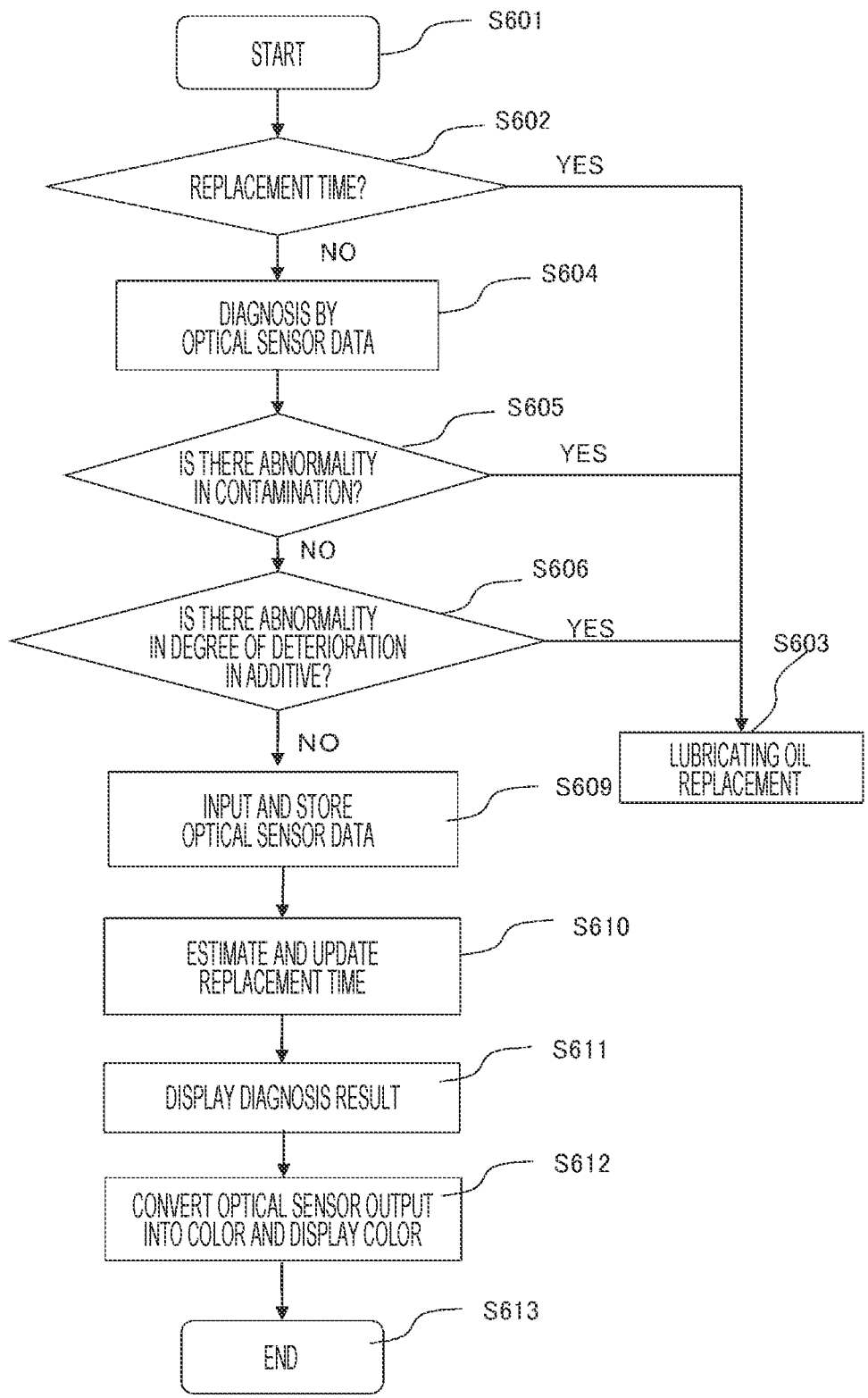
FIG. 13 is a flowchart of lubricating oil diagnosis.

FIG. 13 is a flowchart illustrating lubricating oil diagnosis processing according to the first embodiment. The processing illustrated in FIG. 13 is performed under the control of any of the server 210, the aggregation server 220, and the central server 240 of FIG. 6. In the following example, it is assumed that the central server 240 performs the processing. Functions such as calculation and control are realized by software stored in the storage device of the server being executed by a processor, and thus, predetermined processing is performed in cooperation with other hardware. Functions equivalent to the functions realized by the software can be realized by, for example, hardware such as a field-programmable gate array (FPGA) or an application specific integrated circuit (ASIC).

When the central server 240 performs control, since the plurality of wind power generators 1 are provided under the control of the central server, the following processing is performed for each wind power generator. This processing is basically repeated processing, and a start timing is set by a timer or the like, and for example, the processing is started at 0:00 every day (S601). The central server 240 can also perform the processing at any timing according to an instruction of an operator.

In processing S602, the central server 240 checks a replacement time of the lubricating oil. For an initial value of the replacement time, the remaining lifespan is initially set on, for example, the assumption that the lubricating oil is operating at a design temperature. This replacement time can be updated later in processing S610 based on actual measurement data.

When it is time to replace the lubricating oil, the lubricating oil is replaced in processing S603. Since the lubricating oil replacement is usually a work performed by a worker, the central server 240 performs display and notification for instructing the worker on a time and a target of the replacement.

When it is not time to replace the lubricating oil, the central server 240 diagnoses the properties of the lubricating oil by the sensor data in processing S604. As the sensor data, the temperature, the hydraulic pressure, the concentration of the particles contained in the lubricating oil, and the like can be used in addition to the chromaticity information of the lubricating oil obtained by the optical sensor.

As described with reference to FIG. 9, information on the optical sensor used as the sensor data can reduce the influence of a measurement error due to the bubbles by using information measured after a predetermined time since the rotary machine is substantially stopped. A timing at which the rotary machine 302 is substantially stopped can be known by monitoring the power generation amount. Alternatively, the timing may be detected based on a control signal for stopping the rotary machine 302.

The data measured by the sensor group 304 is sent to the central server 240, and for example, the central server evaluates the characteristics of the lubricating oil by comparing the parameters obtained from the sensors with predetermined reference values. The central server stores, in advance, a correlation between the chromaticity and the additive concentration illustrated in FIGS. 2 to 4, a change in each of the values of R, G, and B when the additive in the lubricating oil is consumed (the additive is decomposed to generate the oxidation product), and a change in each of the values of R, G, and B when the abrasion powder is generated in the lubricating oil and uses the correlation for comparison with the sensor data. As the reference value, the amount of change in the sensor information per predetermined unit time can be used in addition to a predetermined threshold value.

When the diagnosis result is abnormal in processing S605 and S606, the lubricating oil replacement is performed in processing S603. When the diagnosis result is not abnormal, processing S609 is performed. In processing S605, for example, when all the values of R, G, and B of the optical sensor are lower than predetermined threshold values, it is determined that there is a contamination abnormality. However, data of a sensor of the related art may also be used for the contamination abnormality. In S606, it is determined that there is abnormality in a degree of deterioration in the additive when the additive concentration obtained from the chromaticity measured by the optical sensor is lower than the predetermined threshold value by using the correlation between the additive concentration and the chromaticity illustrated in FIGS. 2 to 4. It is also possible to determine that there is abnormality in the degree of deterioration in the additive when the chromaticity is smaller than the predetermined threshold value without obtaining the additive concentration by the chromaticity.

In processing S609, chromaticity measurement data or the like is input to the central server 240, and the data is stored in time series. In processing S610, a deterioration curve is estimated from the chromaticity measurement data stored in time series or the like and the replacement time of the lubricating oil is estimated. When it is necessary to update the deterioration curve, the update is performed.

In processing S611, the diagnosis result is displayed on the display or printed out as necessary. In processing S612, an output of the optical sensor is converted into an appropriate color and displayed at the time of display, and thus, the content can be easily grasped.

It is possible to obtain a deterioration curve distribution of lubricating oil in wind turbines of similar types and a wind turbine group of wind power generation farms under close conditions by accumulating the optical sensor data, and it is possible to create a deterioration prediction curve from learning data. When 60 minutes or more have elapsed after the speed increasing machine is stopped and the sensor data falls in a range of the deterioration prediction curve, the data within the range is preferably used for the deterioration diagnosis.

Even though the speed increasing machine is stopped during the power generation of the wind turbine and 60 minutes or more have elapsed, the optical sensor data may be stabilized at a value lower than the deterioration prediction curve. When such a state is continued, there is a high possibility that contamination such as an increase in water mixing or abrasion powder occurs in addition to the deterioration in the lubricating oil.

Figure 14:
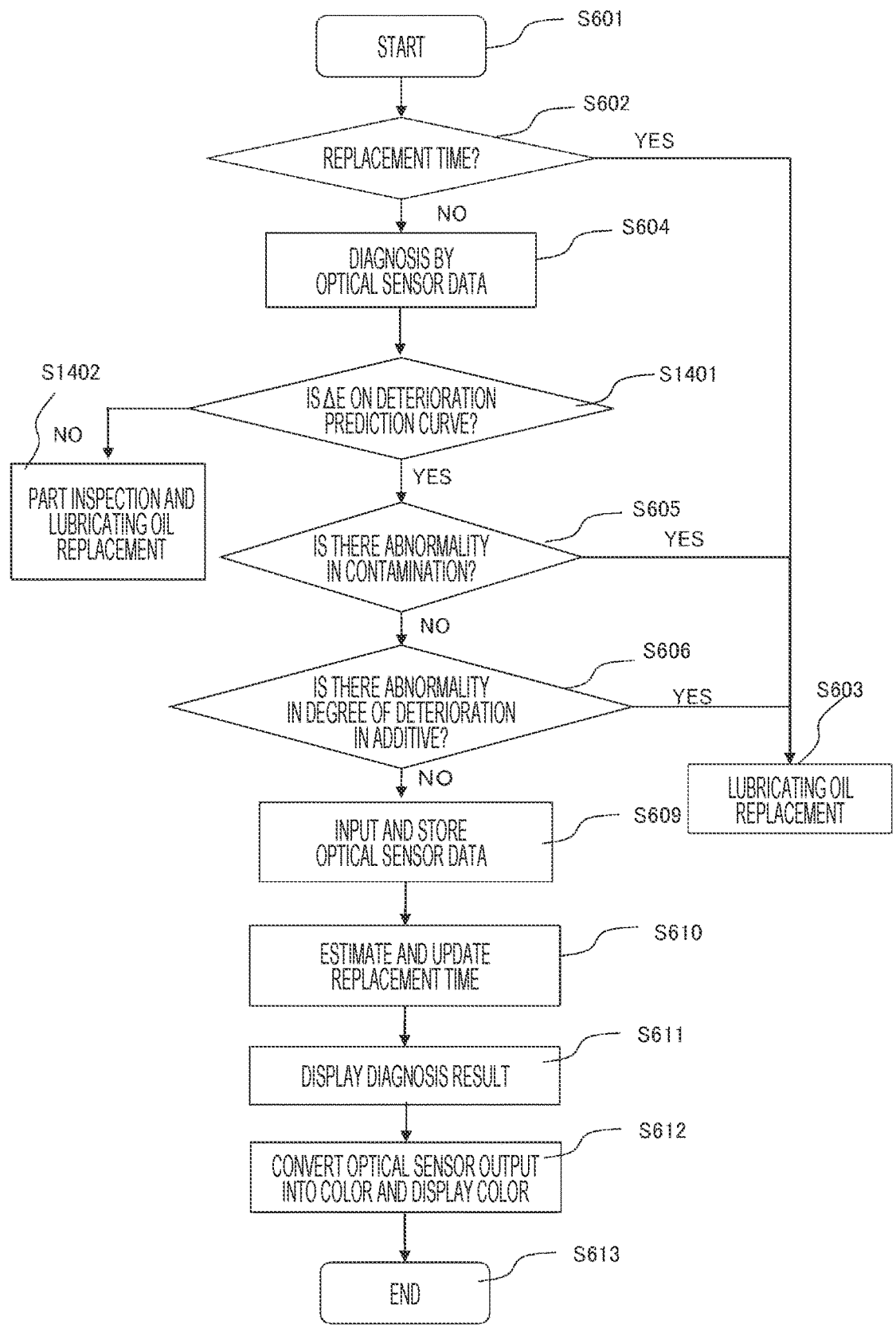
FIG. 14 is another flowchart of the lubricating oil diagnosis.

FIG. 14 is a sensor diagnosis flow using the deterioration prediction curve. When ΔE measured in processing S1401 falls below the deterioration curve in FIGS. 2 to 4, the part inspection and the replacement of lubricating oil are performed in processing S1402.

From the viewpoint of preventive maintenance and planned maintenance of the wind power generator, it is desirable to perform predictive diagnosis on the deterioration of the lubricating oil based on the transition of the concentration of the additive contained in the lubricating oil before it is determined that there is abnormality.

As described above, the lifespan of the lubricating oil can be detected at an early stage by knowing the consumption rate of the additive in the lubricating oil by using the additive concentration measurement result. Thus, the abnormality of the wind power generator can be prevented in advance by maintenance such as appropriate lubricating oil replacement. It is also possible to optimize a replacement cycle of the lubricating oil. The additive concentration can be measured by a simple method, and when the optical sensor is installed in the nacelle, it is also possible to remotely monitor the deterioration in the additive in the lubricating oil online.

In the first embodiment, it is also possible to perform the predictive diagnosis of the contamination due to the abrasion powder and the predictive diagnosis of water mixing online based on the chromaticity measured by the optical sensor. It is also possible to optimize a replacement cycle of the lubricating oil. The additive concentration can be measured by a simple method, and the deterioration in the additive in the lubricating oil can be remotely monitored online by installing the optical sensor in the nacelle.

As described above, it is possible to perform the lubricating oil diagnosis with high accuracy by acquiring sensor data when the air bubble amount in the lubricating oil is equal to or less than a predetermined amount and using the sensor data for diagnosis. Whether or not the air bubble amount in the lubricating oil is equal to or less than the predetermined amount can be determined by directly or indirectly measuring the air bubble amount in the lubricating oil. As direct measurement means, measurement can be performed by a known air bubble ratio measurement device or the like. As indirect measurement means, a relationship between the elapsed time after the rotary machine or the like is stopped and the air bubble amount may be measured in advance, and sensor data after a predetermined time elapses since the rotary machine or the like is stopped may be acquired. Whether or not the rotary machine is stopped can be indirectly detected from the power generation amount in the case of the wind power generator. In the present embodiment, the oil sensor itself may be constantly on as long as a timing of the measurement data to be used can be controlled.

SECOND EMBODIMENT

In the first embodiment (FIG. 7), although the sensor group 304 is provided in a bypass of the main flow path, the sensor group 304 may be provided in the main flow path. For example, in FIG. 7, the sensor group 304 may be installed immediately before the oil filter 305. In a second embodiment, the oil temperature varied from 30° C. to 65° C., and an average flow rate at a position of the sensor group 304 was 100 L per minute. It was confirmed that the diagnosis of the deterioration and contamination of the lubricating oil can be correctly performed by using the sensor data after 60 minutes elapse since the speed increasing machine is stopped due to irregular wind turbine standby and power generation stoppage. It was confirmed that the effect was obtained even though the flow rate was in a range of 5 L to 500 L per minute.

THIRD EMBODIMENT

Figure 15:
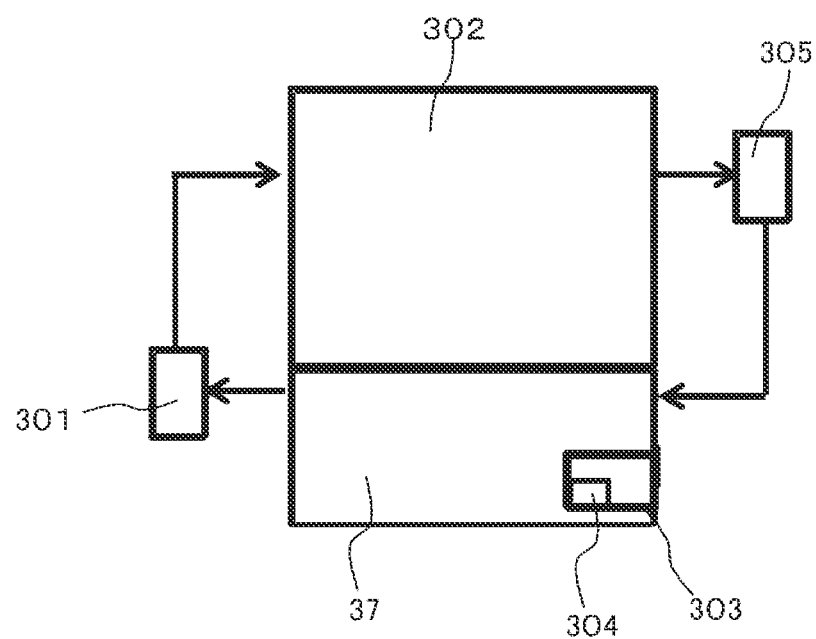
FIG. 15 is a configuration diagram of the rotary machine including the lubricating oil sensor.

FIG. 15 illustrates an example in which the sensor group 304 is provided at a bottom portion of the lubricating oil tank 37 having a depth of 70 cm (at a position 20 cm above a tank bottom surface) connected to the rotary machine 302. Since the air bubbles move upward naturally, it is considered that the air bubble amount at a lower portion is smaller than at an upper portion of the tank. However, when the air bubbles are too close to the bottom of the tank, since a diagnosis result that the solid content in the oil is excessive due to precipitation is obtained or the solid content adheres to the sensor, the sensor group was installed at this position. The oil temperature varied from 10° C. to 60° C. depending on the operation state of the speed increasing machine and the temperature in the nacelle.

During the operation of the speed increasing machine, a large amount of air bubbles were generated in the lubricating oil, but it was confirmed that the diagnosis of the deterioration and contamination of the lubricating oil can be correctly performed by using the sensor data after 70 minutes elapse since the speed increasing machine is stopped due to the irregular wind turbine standby and the power generation stoppage.

FOURTH EMBODIMENT

In the present embodiment, an example in which the contamination diagnosis of the lubricating oil is performed by the optical sensor installed in the speed increasing machine 33 will be described.

The lubricating oil used in the speed increasing machine is several hundred liters or more, and the temperature at which the lubricating oil is used is about 50° C. A lifespan of a general commercially available speed increasing machine oil is 5 years to 7 years, and deterioration progresses slowly. When a plurality of wind turbines of similar types in structure are performing commercial power generation, it is possible to calculate the deterioration rate of the lubricating oil and predict the remaining lifespan of the lubricating oil by accumulating, analyzing, and learning the deterioration diagnosis data by the optical sensor for several years or more.

Figure 16:
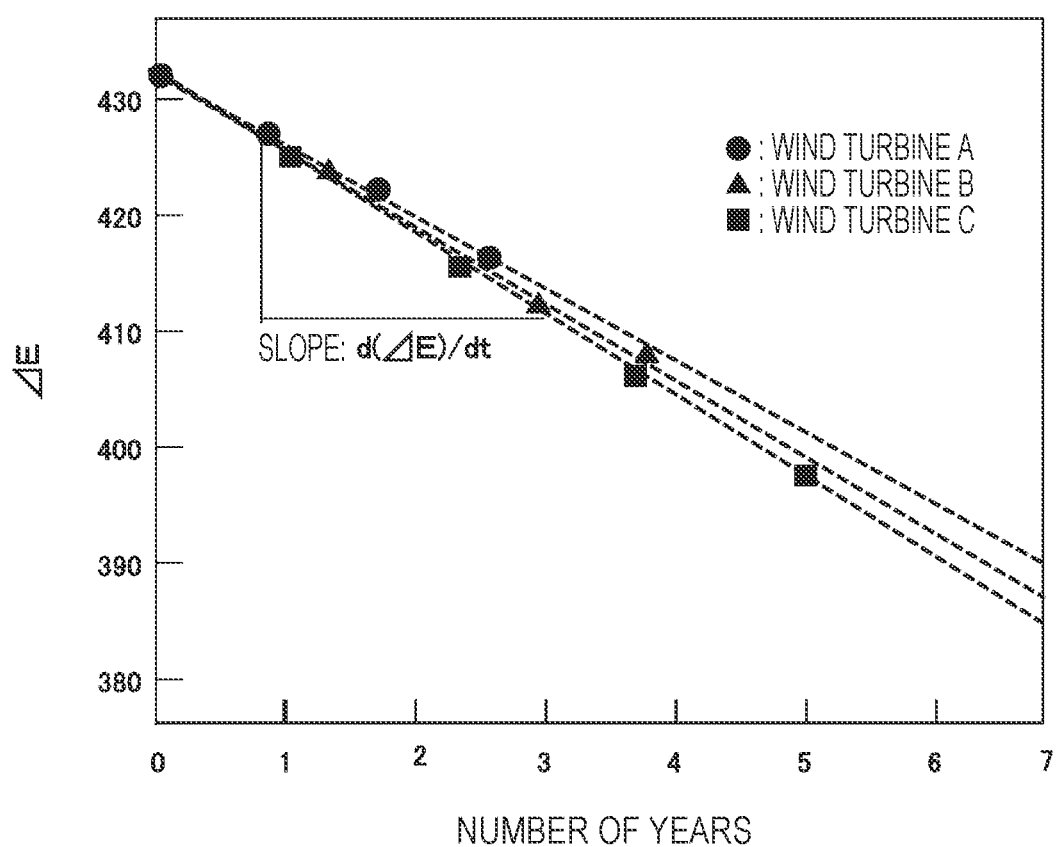
FIG. 16 is a deterioration curve diagram of the lubricating oil using the $\Delta E$ value as an index.

FIG. 16 illustrates deterioration behaviors of lubricating oil in wind turbines (A, B, and C) without contamination of the lubricating oil in the speed increasing machine. A relationship between the number of life years and ΔE can be linearly approximated. A slope $d(\Delta E)/dt$ of this approximate curve does not change over time and falls within a certain range even though the wind turbine is different. Even though the B value having a large correlation with the deterioration in the lubricating oil among the RGB values acquired by the chromaticity sensor was used instead of the ΔE value, the same diagnosis could be performed.

Figure 17:
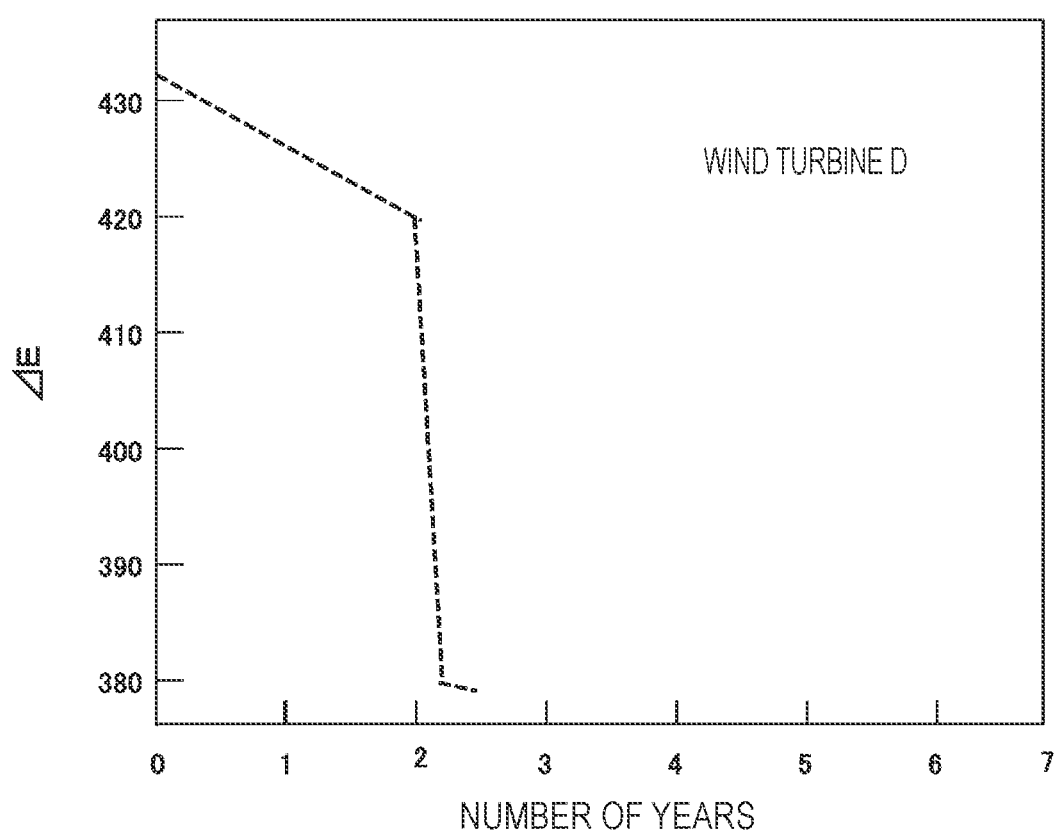
FIG. 17 is a graph of a lubricating oil contamination detection example.

FIG. 17 illustrates an example in which speed increasing machine lubricating oil of a wind turbine D of the same type and in the same farm as the wind turbines A to C is remotely monitored by the optical sensor. After about 2 years from the start of use of the lubricating oil, a rapid decrease in ΔE was exhibited. 100 ml of the speed increasing machine lubricating oil of this wind turbine was collected when 2.6 years elapse, and an appearance inspection was performed. As a result, cloudiness was observed. As a result of analyzing a moisture amount, since 500 ppm of water was contained, the entire lubricating oil amount was replaced immediately thereafter.

FIFTH EMBODIMENT

A fifth embodiment illustrates an example in which the degree of deterioration is obtained by using the B value as an index instead of ΔE.

Figure 18:
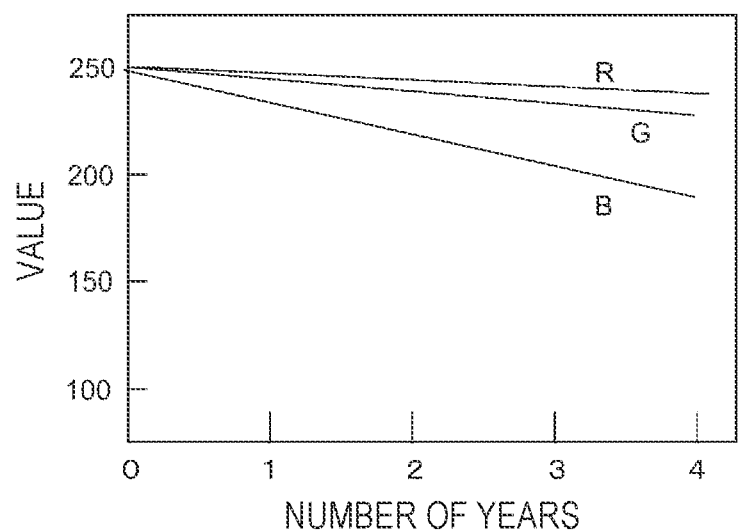
FIG. 18 is a graph representing deterioration in the lubricating oil using the RGB values as indexes.

FIG. 18 is a graph representing deterioration indexes based on color coordinates. A horizontal axis represents time, and a vertical axis represents RGB values. As illustrated in the drawing, in the oxidation deterioration, particularly the B value of RGB decreases. Thus, the deterioration curve can be expressed by using the B value.

Figure 19:
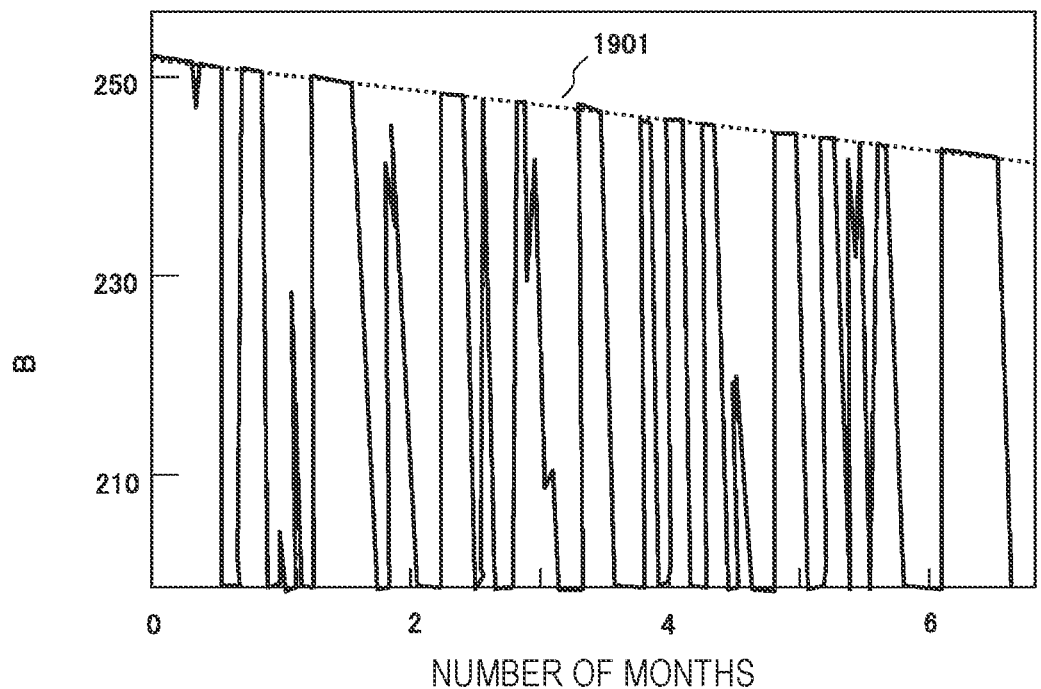
FIG. 19 is a graph representing a monitoring example of the lubricating oil based on the deterioration curve using the B value as the index.

FIG. 19 is a diagram illustrating a deterioration curve 1901 predicted from learning data using a B value. The horizontal axis represents time, and the vertical axis represents a B value. The deterioration curve 1901 can be predicted by using, as an index, the B value by the optical sensor measured at the timing at which the speed increasing machine 33 is stopped.

Figure 20:
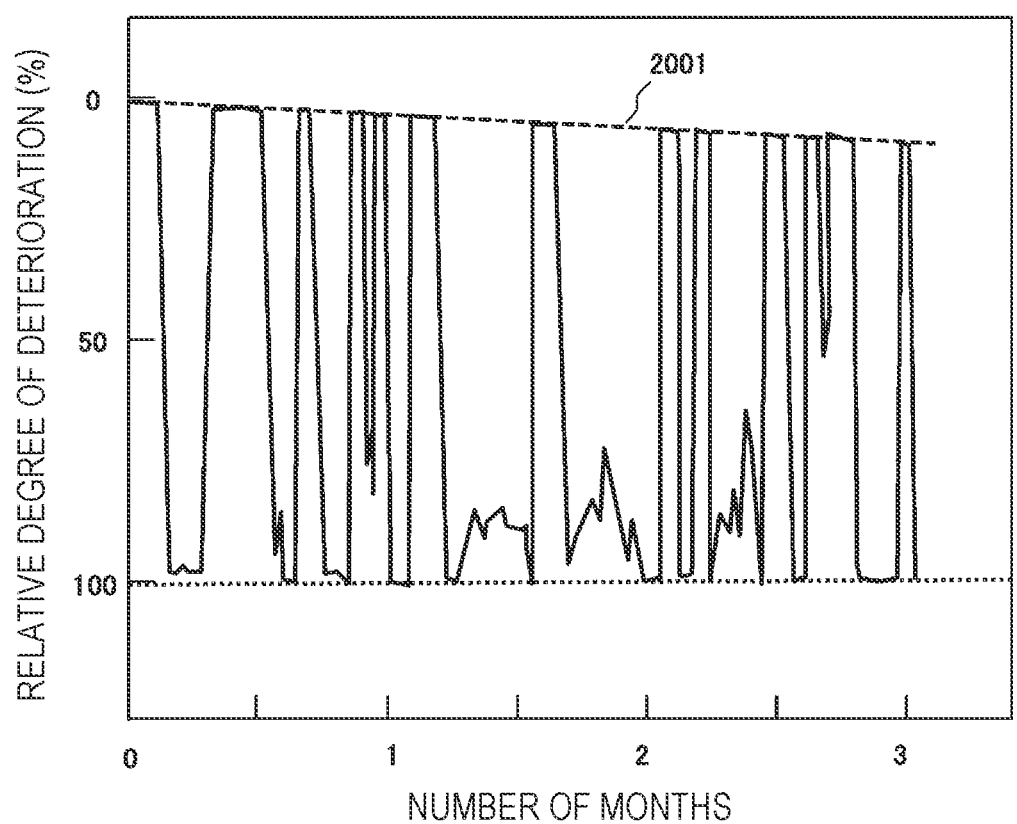
FIG. 20 is a graph representing a relative degree of deterioration in the lubricating oil.

FIG. 20 is a graph representing a deterioration curve 2001 obtained from a deterioration curve 1901 using the B value as the index and using a relative degree of deterioration as the deterioration index. A horizontal axis represents time, and a vertical axis represents the relative degree of deterioration. A new product has a relative degree of deterioration of 0. The relative degree of deterioration can be obtained based on the deterioration curve 1901 predicted from the learning data using the B value and the correlation between the additive characteristics and the chromaticity (in this case, the B value is used instead of ΔE) as illustrated in FIGS. 2 to 4.

SIXTH EMBODIMENT

An example of predictive diagnosis using a deterioration curve based on past data obtained by a chromaticity sensor will be described. Here, an example in which a chromaticity sensor is used as the sensor group 304 by using the system configuration of the first embodiment is illustrated.

Figure 21:
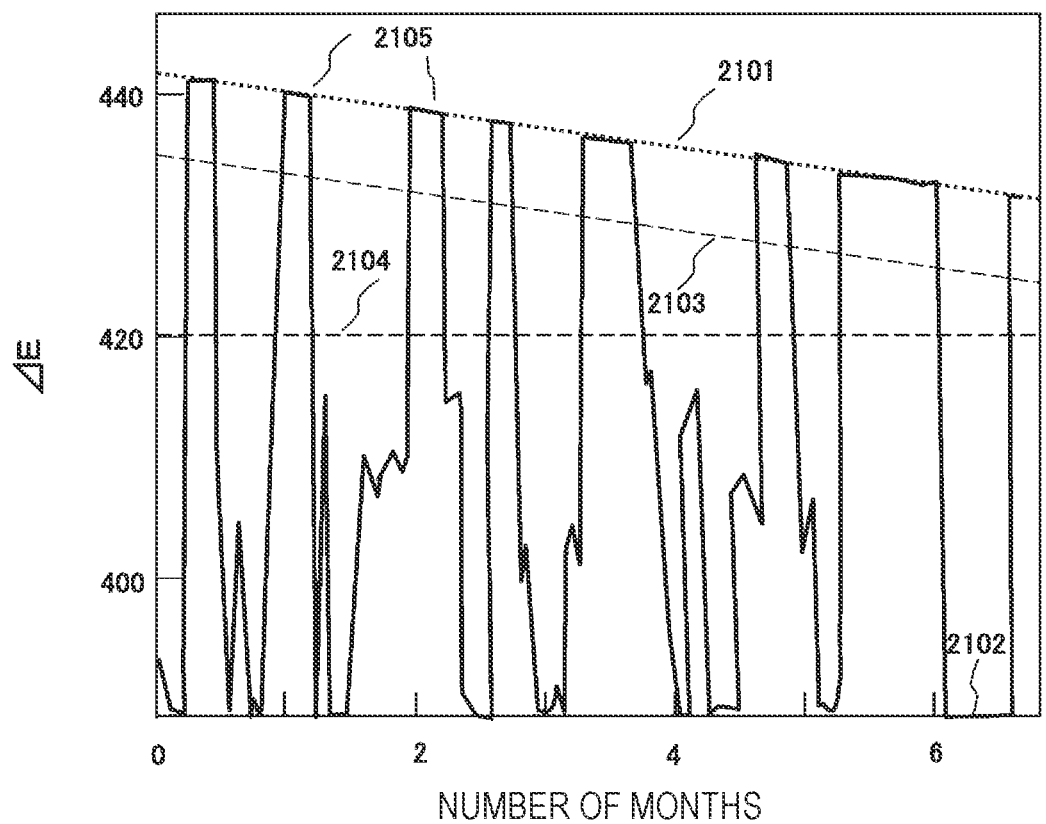
FIG. 21 is a graph representing a lubricating oil deterioration detection example using a deterioration prediction curve.

FIG. 21 is a graph in which a horizontal axis represents elapsed time and a vertical axis represents ΔE obtained by the chromaticity sensor. In general, since the deterioration in the lubricating oil progresses at a constant rate, the deterioration curve 2101 can be obtained from the past value of ΔE. The example of FIG. 21 illustrates an example in which the deterioration in the lubricating oil normally progresses.

As described in the first embodiment, since an error occurs in the data by the chromaticity sensor due to the generation of the bubbles, for example, a low ΔE value may be acquired as represented in data 2102 due to the influence of the bubbles. A decrease in the ΔE value due to the bubbles is recovered after a predetermined time after the rotary machine is stopped. Thus, accurate diagnosis can be performed by acquiring the sensor data when the value of the deterioration index (for example, ΔE) based on the sensor data of the chromaticity sensor is within a range not influenced by the bubbles and using the sensor data for predictive diagnosis. For example, when there is sensor data between the deterioration curve 2101 and a threshold value, the data is used to determine deterioration.

As the threshold value, a threshold value 2103 obtained by subtracting a predetermined value from the deterioration curve 2101 with the deterioration curve as an upper limit can be used. Alternatively, a constant value such as the threshold value 2104 can be used. Since the threshold value varies depending on the type of the machine or the type of the lubricating oil, for example, as illustrated in FIG. 10, the relationship between the air bubble amount and ΔE may be actually measured to set a value that can identify the presence or absence of the influence of the bubbles.

More accurate predictive diagnosis can be performed by using data of a portion 2105 where ΔE is stable without being influenced by the bubbles in the vicinity of the deterioration curve 2101. That is, the accurate deterioration curve 2101 can be obtained by using the data of the portion 2105 where ΔE is stable when the deterioration curve 2101 is generated. Whether or not ΔE is stable may be determined by evaluating a temporal variation amount of data.

The data acquisition method limited to the predetermined range can be used in combination with the method for acquiring the data after the required time elapses since the rotary machine is stopped described in the first embodiment.

Figure 22:
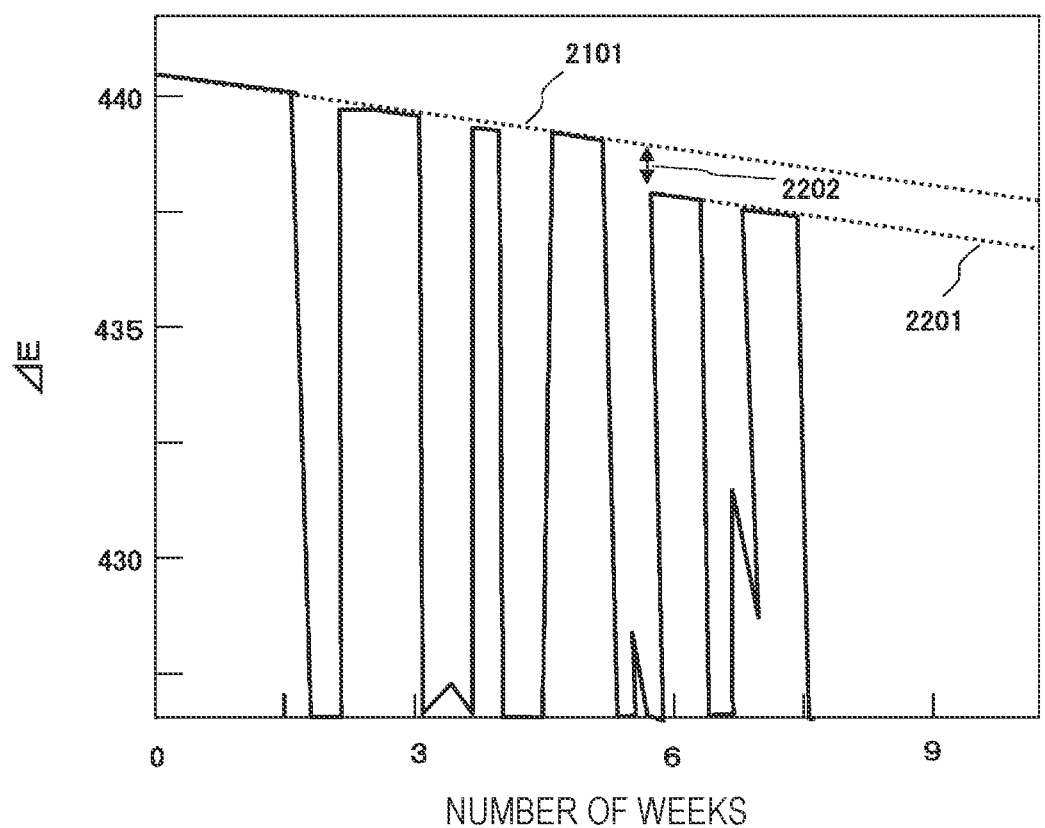
FIG. 22 is a graph representing a lubricating oil contamination detection example using the deterioration prediction curve.

FIG. 22 illustrates an example in which the lubricating oil of the speed increasing machine is contaminated due to an increase in the abrasion powder. A horizontal axis represents the elapsed time, and a vertical axis represents the value of ΔE. With respect to the deterioration curve 2101 obtained by analyzing and learning the past measurement data of the speed increasing machine oil, the deterioration curve 2201 based on the measured value deviates from the deterioration curve 2101 predicted from the learning data even though the speed increasing machine is stopped for 1 hour or more at a point in time of 6 months after the start of use. Thereafter, since the deviation was continued, it was determined that the deterioration curve 2201 based on the measured value was shifted by a change amount 2202 due to the contamination of the lubricating oil.

Thus, when 100 ml of the speed increasing machine oil was collected at a point in time at which 7.5 months elapse and particle number measurement by a particle counter and ferrography analysis were performed, since an abnormal increase in the number of solid particles and a large number of abnormal abrasion powder of the gear were detected, the speed increasing machine was inspected when 9 months elapse, and a loss of the gear was confirmed.

As illustrated in FIG. 22, it is possible to distinguish between the deterioration in the lubricating oil and the contamination of the lubricating oil in the predictive diagnosis. In general, the deterioration in the lubricating oil progresses at a predetermined rate in terms of time as indicated by the deterioration curves 2101 and 2201. On the other hand, since the contamination of the lubricating oil occurs due to mixing of water or foreign matter, the measured value rapidly changes as indicated by the change amount 2202.

SEVENTH EMBODIMENT

Figure 23:
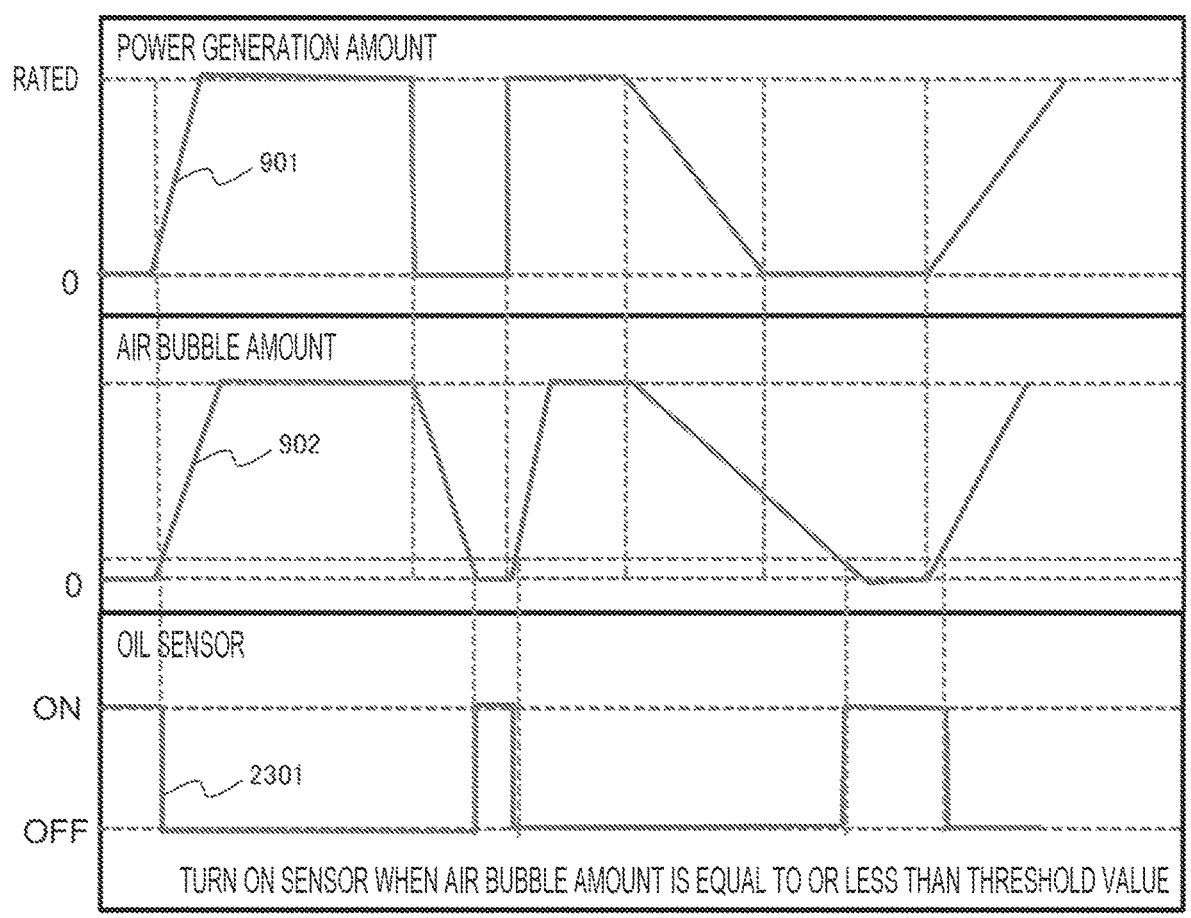
FIG. 23 is a sequence diagram for acquiring data by turning on power of an optical sensor after air bubbles disappear since the wind turbine is stopped.

FIG. 23 illustrates an example in which an optical chromaticity sensor is installed in a speed increasing machine of a 5 MW wind turbine having the speed increasing machine 33, and the chromaticity sensor is powered on after the power generation amount of the wind turbine is 0, that is, after 60 minutes elapse since the speed increasing machine is stopped, and measurement is performed. On and off control of the oil sensor is performed according to control signal 2301, and data of ON timing is used.

As illustrated in FIG. 23, it is possible to reduce the amount of measurement data and to reduce an electrical deterioration of the chromaticity sensor over time by using a measurement sequence in which the oil sensor is repeatedly turned on and off.

In the above embodiment, although the chromaticity sensor which is the optical sensor has been described as an example, the present invention is effective for sensors in which measurement values can be influenced by the air bubbles, such as a particle counter, a dielectric constant sensor, an electrical conductivity sensor, and a viscosity sensor, in addition to the chromaticity sensor.

In the specific embodiment, the characteristics of the lubricating oil can be accurately measured by performing the measurement under the condition of a small amount of bubbles.

The present invention is not limited to the aforementioned embodiments, and includes various modification examples. For example, the aforementioned embodiments are described in detail in order to facilitate easy understanding of the present invention, and are not limited to necessarily include all the described components. Furthermore, some of the components of a certain embodiment can be substituted into the components of another embodiment, and the components of another embodiment can be added to the component of a certain embodiment. Furthermore, another component can be added, removed, and substituted to, from, and into some of the components of the aforementioned embodiments.

For example, in the above-described embodiments, although the wind power generator has been described as the example of the rotary machine, the present invention can also be applied to deterioration diagnosis of an additive of lubricating oil of a rotary machine such as a nuclear power generator, a thermal power generator, a geared motor, a railway vehicle wheel flange, an air compressor, a transformer, a movable plant machine, or a large-scaled pump machine.

REFERENCE SIGNS LIST 1 wind power generator
2 tower
3 nacelle
4 hub
5 blade
33 speed increasing machine
34 power generator
210 server
220 aggregation server
230 network
240 central server
301 lubricating oil supply device
302 rotary machine
303 measurement unit
304 sensor group
901 power generation amount
902 air bubble amount
903 oil sensor data ΔE

The invention claimed is:

1. A diagnosis system of lubricating oil of a wind power generator, comprising:
a nacelle of the wind power generator;
a lubricating oil utilization device disposed within the nacelle;
a lubricating oil tank, disposed within the nacelle, for storing lubricating oil to be supplied to the lubricating oil utilization device;
a circulation line, within the nacelle, through which lubricating oil circulated between the lubricating oil tank and the lubricating oil utilization device flows; and
a sensor, disposed within the nacelle, which measures characteristics of the lubricating oil; and
a server, disposed within the nacelle, that is coupled to the sensor and is configured to:
acquire sensor data of the sensor, which is used for diagnosis after more than a predetermined time elapses since the lubricating oil utilization device enters a stoppage state, and
determine whether a value of the data of the sensor is below a predetermined threshold,
upon determining the value of the data of the sensor is below the predetermined threshold, present a notification indicating replacement of the lubricating oil is necessary, and
upon determining the value of the data of the sensor is not below the predetermined threshold, estimate a replacement time for replacing the lubricating oil.

2. The diagnosis system of lubricating oil according to claim 1,
wherein the stoppage state is unexpected stoppage due to an external factor.

3. The diagnosis system of lubricating oil according to claim 1,
wherein the sensor is one or more sensors selected from among a chromaticity sensor, a particle counter, a dielectric constant sensor, an electrical conductivity sensor, and a viscosity sensor.

4. The diagnosis system of lubricating oil according to claim 1,
wherein the lubricating oil utilization device is a speed increasing machine of the wind power generator.

5. The diagnosis system of lubricating oil according to claim 4,
wherein the acquisition of the data of the sensor is performed after more than a predetermined time elapses since the speed increasing machine enters an unexpected stoppage state due to an external factor.

6. The diagnosis system of lubricating oil according to claim 5,
wherein the acquisition of the data of the sensor is performed after more than a predetermined time elapses since the speed increasing machine enters a stoppage state for a wind condition of a cut-out wind speed or more.

7. The diagnosis system of lubricating oil according to claim 4,
wherein the sensor is a chromaticity sensor, and
wherein the acquisition of the data of the chromaticity sensor is performed when a value of a deterioration index based on the data of the chromaticity sensor is in a predetermined range.

8. A diagnosis system of lubricating oil of a wind power generator, comprising:
a nacelle of the wind power generator;
a lubricating oil utilization device disposed within the nacelle;
a lubricating oil tank, disposed within the nacelle, for storing lubricating oil to be supplied to the lubricating oil utilization device;
a circulation line, within the nacelle, through which lubricating oil circulated between the lubricating oil tank and the lubricating oil utilization device flows; and
a chromaticity sensor, disposed within the nacelle, which measures characteristics of the lubricating oil;

a sensor, disposed within the nacelle, which measures characteristics of the lubricating oil; and a server, disposed within the nacelle, that is coupled to the sensor and is configured to:

determine whether a value of a deterioration index based on sensor data of the chromaticity sensor is in a predetermined range, upon determining the value is in the predetermined range, acquire sensor data of the sensor, determine whether a value of the data of the sensor is below a predetermined threshold, upon determining the value of the data of the sensor is below the predetermined threshold, present a notification indicating replacement of the lubricating oil is necessary, and upon determining the value of the data of the sensor is not below the predetermined threshold, estimate a replacement time for replacing the lubricating oil.

9. The diagnosis system of lubricating oil according to claim 8, wherein the deterioration index is a deterioration index based on ΔE by the chromaticity sensor.

10. The diagnosis system of lubricating oil according to claim 8, wherein the deterioration index is a deterioration index based on a B value by the chromaticity sensor.

11. The diagnosis system of lubricating oil according to claim 8, wherein the predetermined range is a range which uses, as an upper limit, a deterioration curve of the lubricating oil obtained from past data and is between the deterioration curve and a threshold value.

12. A diagnosis method of lubricating oil of a wind power generator, which includes a nacelle of the wind power generator, a lubricating oil utilization device disposed within the nacelle, a lubricating oil tank, disposed within the nacelle, for storing lubricating oil to be supplied to the lubricating oil utilization device, a circulation line through which lubricating oil circulated between the lubricating oil tank and the lubricating oil utilization device flows, a chromaticity sensor, disposed within the nacelle, which measures characteristics of the lubricating oil, a sensor, disposed within the nacelle, which measures characteristics of the lubricating oil, and a server, disposed within the nacelle, the method comprising:

using the chromaticity sensor to measure characteristics of the lubricating oil;

determining whether a value of a deterioration index based on sensor data of the chromaticity sensor is in a predetermined range;

upon determining the value is in the predetermined range, acquire sensor data of the sensor;

determine whether a value of the data of the sensor is below a predetermined threshold;

upon determining the value of the data of the sensor is below the predetermined threshold, present a notification indicating replacement of the lubricating oil is necessary; and upon determining the value of the data of the sensor is not below the predetermined threshold, estimate a replacement time for replacing the lubricating oil.

13. The diagnosis method of lubricating oil according to claim 12, wherein the stoppage state is an unexpected stoppage due to an external factor.

14. The diagnosis method of lubricating oil according to claim 13, wherein the apparatus is a speed increasing machine of a wind power generator, and wherein the unexpected stoppage state occurs when the speed increasing machine enters a stoppage state for a wind condition of a cut-out wind speed or more.

15. The diagnosis method of lubricating oil according to claim 12, wherein a deterioration curve of the lubricating oil is obtained by using a B value based on the data of the chromaticity sensor.

\* \* \* \* \*